(12) United States Patent
Chokhawala et al.

(10) Patent No.: US 9,410,135 B2
(45) Date of Patent: Aug. 9, 2016

(54) **THERMOPHILIC MUTANTS OF *TRICHODERMA REESEI* ENDOGLUCANASE I**

(75) Inventors: Harshal Akshay Chokhawala, Berkeley, CA (US); Tae-Wan Kim, Albany, CA (US); Harvey W. Blanch, San Francisco, CA (US); Douglas S. Clark, Orinda, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 473 days.

(21) Appl. No.: 13/822,623

(22) PCT Filed: Aug. 11, 2011

(86) PCT No.: PCT/US2011/047361
§ 371 (c)(1),
(2), (4) Date: May 8, 2013

(87) PCT Pub. No.: WO2012/036810
PCT Pub. Date: Mar. 22, 2012

(65) Prior Publication Data
US 2015/0037845 A1    Feb. 5, 2015

Related U.S. Application Data

(60) Provisional application No. 61/383,240, filed on Sep. 15, 2010, provisional application No. 61/422,081, filed on Dec. 10, 2010.

(51) Int. Cl.
*C12N 9/42* (2006.01)
*C12P 7/10* (2006.01)
*C12P 19/14* (2006.01)

(52) U.S. Cl.
CPC .......... *C12N 9/2437* (2013.01); *C12N 9/244* (2013.01); *C12P 7/10* (2013.01); *C12P 19/14* (2013.01);
(Continued)

(58) Field of Classification Search
CPC ........ C12N 9/2437; C12N 9/244; C12P 7/10; C12P 19/14
See application file for complete search history.

(56) References Cited

U.S. PATENT DOCUMENTS 7,824,884 B2 * 11/2010 Harris et al. ................. 435/69.1
7,906,309 B2 *  3/2011 Emalfarb et al. ............. 435/200
(Continued)

FOREIGN PATENT DOCUMENTS

| JP | 2006-515506 A | 6/2006 |
| JP | 2007-517499 A | 7/2007 |

(Continued)

OTHER PUBLICATIONS

Kvesitadze, E.G., et al., 1995, "Isolation and properties of a thermostable endoglucanase from a thermophilic mutant strain of Thielavia terrestris", Applied Biochemistry and Biotechnology, vol. 50, pp. 137-143.*

(Continued)

*Primary Examiner* — Manjunath Rao
*Assistant Examiner* — William W Moore
(74) *Attorney, Agent, or Firm* — Morrison & Foerster LLP

(57) ABSTRACT

The present disclosure relates to mutant thermostable glycosyl hydrolases family 7 enzymes, including mutant *Trichoderma reesei* endoglucanase I. In particular, the present disclosure relates to mutant thermostable enzymes, compositions containing the enzymes, and methods of use thereof.

19 Claims, 15 Drawing Sheets

(52) U.S. Cl.
CPC . *C12Y 302/01004* (2013.01); *C12Y 302/01006* (2013.01); *C12P 2201/00* (2013.01); *Y02E 50/16* (2013.01)

(56) References Cited

U.S. PATENT DOCUMENTS

| | | | |
|---|---|---|---|
| 8,063,267 B2 * | 11/2011 | Harris et al. | 800/288 |
| 8,637,293 B2 * | 1/2014 | Adney et al. | 435/201 |
| 2003/0177530 A1 | 9/2003 | Varghese et al. | |
| 2005/0054039 A1 * | 3/2005 | Goedegebuur et al. | 435/69.1 |
| 2005/0277172 A1 | 12/2005 | Day et al. | |
| 2009/0019608 A1 | 1/2009 | Lopez de Leon et al. | |
| 2009/0220480 A1 | 9/2009 | Gray et al. | |
| 2011/0319294 A1 * | 12/2011 | Arnold et al. | 506/11 |

FOREIGN PATENT DOCUMENTS

| | | |
|---|---|---|
| JP | 2007-534294 A | 11/2007 |
| JP | 2011-125341 A | 6/2011 |
| JP | 2011-152136 A | 8/2011 |
| WO | 2004/016760 A2 | 2/2004 |
| WO | 2005/001065 A2 | 1/2005 |
| WO | 2010/088387 A1 | 8/2010 |

OTHER PUBLICATIONS

Kleywegt et al., "The Crystal Structure of the Catalytic Core Domain of Endoglucanase I from Trichoderma Reesei at 3.6 Å Resolution, and a Comparison with Related Enzymes", Journal of Molecular Biology, vol. 272, No. 3, Sep. 26, 1997, pp. 383-397.

Extended European Search Report (includes Supplementary European Search Report and Search Opinion) received for European Patent Application No. 11825612.2 mailed on Jan. 7, 2014, 12 pages.

"Endoglucanase EG-1", UniProt Accession No. Q7S390, Available Online at <http://www.uniprot.org/uniprot/Q7S390.txt?version=42>, Dec. 15, 2003, 1 page.

"Endoglucanase I", Uniprot Accession No. A2TDD6, Available Online at <http://www.uniprot.org/uniprot/A2TDD6.txt>, Mar. 6, 2007, 1 page.

Ahn et al., "Molecular Cloning and Characterization of Cel2 from the Fungus Cochlibolus Carbonum", Bioscience Biotechnology Biochemistry, vol. 65, No. 6, 2001, pp. 1406-1411.

Voutilainen et al., "Heterologous Expression of Melanocarpus Albomyces Cellobiohydrolase Cel7B, and Random Mutagenesis to Improve Its Thermostability", Enzyme and Microbial Technology, vol. 41, 2007, pp. 234-243.

Invitation to Pay Additional Fees received for PCT Patent Application No. PCT/US2011/047361, mailed on Dec. 29, 2011, 2 pages.

International Search Report and Written Opinion received for PCT Patent Application No. PCT/US2011/047361, mailed on Mar. 16, 2012, 12 pages.

International Preliminary Report on Patentability received for PCT Patent Application No. PCT/US2011/047361, mailed on Mar. 19, 2013, 8 pages.

Office Action received for Japanese Patent Application No. 2013-529155, mailed on Jul. 7, 2015, 7 pages (4 pages of English Translation and 3 pages of JPOA).

Boer et al., "The Relationship Between Thermal Stability and pH Optimum Studied with Wild-Type and Mutant Trichoderma Reesei Cellobiohydrolase Cel7A", Eur J Biochem. vol. 270, 2003, pp. 841-848.

Voutilainen et al., "Improving the Thermostability and Activity of Melanocarpus Albomyces Cellobiohydrolase Cel7B", Applied Microbiology Biotechnology, vol. 83, No. 2, 2009, pp. 261-272.

* cited by examiner

CMC ASSAY OF EGI AT pH 4.8

MULTIPLEXING WITH 4 CLONES PER WELL POSSIBLE

```
                        SEQUENCE LISTING

<160> NUMBER OF SEQ ID NOS: 19

<210> SEQ ID NO 1
<211> LENGTH: 437
<212> TYPE: PRT
<213> ORGANISM: Trichoderma reesei

<400> SEQUENCE: 1

Gln Gln Pro Gly Thr Ser Thr Pro Glu Val His Pro Lys Leu Thr Thr
 1               5                  10                  15

Tyr Lys Cys Thr Lys Ser Gly Gly Cys Val Ala Gln Asp Thr Ser Val
             20                  25                  30

Val Leu Asp Trp Asn Tyr Arg Trp Met His Asp Ala Asn Tyr Asn Ser
         35                  40                  45

Cys Thr Val Asn Gly Gly Val Asn Thr Thr Leu Cys Pro Asp Glu Ala
     50                  55                  60

Thr Cys Gly Lys Asn Cys Phe Ile Glu Gly Val Asp Tyr Ala Ala Ser
 65                  70                  75                  80

Gly Val Thr Thr Ser Gly Ser Ser Leu Thr Met Asn Gln Tyr Met Pro
                 85                  90                  95

Ser Ser Ser Gly Gly Tyr Ser Ser Val Ser Pro Arg Leu Tyr Leu Leu
            100                 105                 110

Asp Ser Asp Gly Glu Tyr Val Met Leu Lys Leu Asn Gly Gln Glu Leu
        115                 120                 125

Ser Phe Asp Val Asp Leu Ser Ala Leu Pro Cys Gly Glu Asn Gly Ser
    130                 135                 140

Leu Tyr Leu Ser Gln Met Asp Glu Asn Gly Gly Ala Asn Gln Tyr Asn
145                 150                 155                 160

Thr Ala Gly Ala Asn Tyr Gly Ser Gly Tyr Cys Asp Ala Gln Cys Pro
                165                 170                 175

Val Gln Thr Trp Arg Asn Gly Thr Leu Asn Thr Ser His Gln Gly Phe
            180                 185                 190

Cys Cys Asn Glu Met Asp Ile Leu Glu Gly Asn Ser Arg Ala Asn Ala
        195                 200                 205

Leu Thr Pro His Ser Cys Thr Ala Thr Ala Cys Asp Ser Ala Gly Cys
    210                 215                 220

Gly Phe Asn Pro Tyr Gly Ser Gly Tyr Lys Ser Tyr Tyr Gly Pro Gly
225                 230                 235                 240

Asp Thr Val Asp Thr Ser Lys Thr Phe Thr Ile Ile Thr Gln Phe Asn
                245                 250                 255

Thr Asp Asn Gly Ser Pro Ser Gly Asn Leu Val Ser Ile Thr Arg Lys
            260                 265                 270

Tyr Gln Gln Asn Gly Val Asp Ile Pro Ser Ala Gln Pro Gly Gly Asp
        275                 280                 285

Thr Ile Ser Ser Cys Pro Ser Ala Ser Ala Tyr Gly Gly Leu Ala Thr
    290                 295                 300

Met Gly Lys Ala Leu Ser Ser Gly Met Val Leu Val Phe Ser Ile Trp
305                 310                 315                 320
```

```
            Asn Asp Asn Ser Gln Tyr Met Asn Trp Leu Asp Ser Gly Asn Ala Gly
                        325                 330                 335

Pro Cys Ser Ser Thr Glu Gly Asn Pro Ser Asn Ile Leu Ala Asn Asn
                    340                 345                 350

Pro Asn Thr His Val Val Phe Ser Asn Ile Arg Trp Gly Asp Ile Gly
                355                 360                 365

Ser Thr Thr Asn Ser Thr Ala Pro Pro Pro Pro Ala Ser Ser Thr
            370                 375                 380

Thr Phe Ser Thr Thr Arg Arg Ser Ser Thr Ser Ser Ser Pro Ser
        385                 390                 395                 400

Cys Thr Gln Thr His Trp Gly Gln Cys Gly Gly Ile Gly Tyr Ser Gly
                        405                 410                 415

Cys Lys Thr Cys Thr Ser Gly Thr Thr Cys Gln Tyr Ser Asn Asp Tyr
                    420                 425                 430

Tyr Ser Gln Cys Leu
                435

<210> SEQ ID NO 2
<211> LENGTH: 30
<212> TYPE: DNA
<213> ORGANISM: Artificial Sequence
<220> FEATURE:
<223> OTHER INFORMATION: Synthetic Construct

<400> SEQUENCE: 2
aaaaaacata tgcaacaacc gggcacctcc                                    30

<210> SEQ ID NO 3
<211> LENGTH: 33
<212> TYPE: DNA
<213> ORGANISM: Artificial Sequence
<220> FEATURE:
<223> OTHER INFORMATION: Synthetic Construct

<400> SEQUENCE: 3
aaaaaagtcg acttacagac attgcgagta gta                                33

<210> SEQ ID NO 4
<211> LENGTH: 59
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: 22, 25, 28, 31
<223> OTHER INFORMATION: n = A,T,C or G

<400> SEQUENCE: 4
ggcgtcgata ttccgtccgc andtndtndt ndtgacacca tctctagttg cccgtcagc    59

<210> SEQ ID NO 5
<211> LENGTH: 59
<212> TYPE: DNA
<213> ORGANISM: Artificial Sequence
<220> FEATURE:
<223> OTHER INFORMATION: Synthetic Construct

<400> SEQUENCE: 5
gctgacgggc aactagagat ggtgtcahma hmahmahmtg cggacggaat atcgacgcc    59

<210> SEQ ID NO 6
<211> LENGTH: 43
<212> TYPE: DNA
```

```
<213> ORGANISM: Artificial Sequence
<220> FEATURE:
<223> OTHER INFORMATION: Synthetic Construct
<221> NAME/KEY: misc_feature
<222> LOCATION: 19, 20, 22, 23
<223> OTHER INFORMATION: n = A,T,C or G

<400> SEQUENCE: 6
tcagcatcgg cctacggcnn knnkgcaacc atgggcaaag ctc                    43

<210> SEQ ID NO 7
<211> LENGTH: 43
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: 21, 22, 24, 25
<223> OTHER INFORMATION: n = A,T,C or G

<400> SEQUENCE: 7
gagctttgcc catggttgcm nnmnngccgt aggccgatgc tga                    43

<210> SEQ ID NO 8
<211> LENGTH: 44
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: 18, 19, 24, 25
<223> OTHER INFORMATION: n = A,T,C or G

<400> SEQUENCE: 8
cgcgtctgta tctgctgnnk tctnnkggcg aatacgtgat gctg                   44

<210> SEQ ID NO 9
<211> LENGTH: 44
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: 20, 21, 26, 27
<223> OTHER INFORMATION: n = A,T,C or G

<400> SEQUENCE: 9
cagcatcacg tattcgccmn nagamnncag cagatacaga cgcg                   44

<210> SEQ ID NO 10
<211> LENGTH: 28
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: 14, 15
<223> OTHER INFORMATION: n = A,T,C or G

<400> SEQUENCE: 10
caaatcctat tacnnkccgg gtgatacc                                     28

<210> SEQ ID NO 11
<211> LENGTH: 28
<212> TYPE: DNA
<213> ORGANISM: Artificial Sequence
<220> FEATURE:
<223> OTHER INFORMATION: Synthetic Construct
<221> NAME/KEY: misc_feature
```

<222> LOCATION: 14, 15
<223> OTHER INFORMATION: n = A,T,C or G

<400> SEQUENCE: 11
ggtatcaccc ggmnngtaat aggatttg                                            28

<210> SEQ ID NO 12
<211> LENGTH: 31
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: 15, 16
<223> OTHER INFORMATION: n = A,T,C or G

<400> SEQUENCE: 12
gtttcaaccc gtatnnkagt ggttacaaat c                                        31

<210> SEQ ID NO 13
<211> LENGTH: 31
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: 16, 17
<223> OTHER INFORMATION: n = A,T,C or G

<400> SEQUENCE: 13
gatttgtaac cactmnnata cgggttgaaa c                                        31

<210> SEQ ID NO 14
<211> LENGTH: 29
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: 15, 16
<223> OTHER INFORMATION: n = A,T,C or G

<400> SEQUENCE: 14
caatttggaa cgatnnktcg cagtatatg                                           29

<210> SEQ ID NO 15
<211> LENGTH: 29
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: 14, 15
<223> OTHER INFORMATION: n = A,T,C or G

<400> SEQUENCE: 15
catatactgc gamnnatcgt tccaaattg                                           29

<210> SEQ ID NO 16
<211> LENGTH: 25
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: 13, 14
<223> OTHER INFORMATION: n = A,T,C or G

<400> SEQUENCE: 16

-continued

```
gacaccatct ctnnktgccc gtcag                                    25

<210> SEQ ID NO 17
<211> LENGTH: 25
<212> TYPE: DNA
<213> ORGANISM: Artificial Sequence
<220> FEATURE:
<223> OTHER INFORMATION: Synthetic Construct
<221> NAME/KEY: misc_feature
<222> LOCATION: 12, 13
<223> OTHER INFORMATION: n = A,T,C or G

<400> SEQUENCE: 17
ctgacgggca mnnagagatg gtgtc                                    25

<210> SEQ ID NO 18
<211> LENGTH: 35
<212> TYPE: DNA
<213> ORGANISM: Artificial Sequence
<220> FEATURE:
<223> OTHER INFORMATION: Synthetic Construct

<400> SEQUENCE: 18
tcgatcccgc gaaattaata cgactcacta taggg                         35

<210> SEQ ID NO 19
<211> LENGTH: 26
<212> TYPE: DNA
<213> ORGANISM: Artificial Sequence
<220> FEATURE:
<223> OTHER INFORMATION: Synthetic Construct

<400> SEQUENCE: 19
caaaaaaccc ctcaagaccc gtttag                                   26
```

THERMOPHILIC MUTANTS OF *TRICHODERMA REESEI* ENDOGLUCANASE I

CROSS REFERENCE TO RELATED APPLICATIONS

This is a U.S. National Phase patent application of PCT/US2011/047361, filed Aug. 11, 2011, which claims the benefit of U.S. Provisional Application No. 61/383,240, filed Sep. 15, 2010, and U.S. Provisional Application No. 61/422,081, filed Dec. 10, 2010, the disclosures of which are hereby incorporated by reference in their entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 677792001100SEQLISTING.TXT, date recorded: Mar. 12, 2013, size: 14 KB).

FIELD

The present disclosure relates to thermostable glycosyl hydrolases family 7 enzymes which contain amino acid mutations, including endoglucanases from *Trichoderma reesei*. In particular, the present disclosure relates to compositions including a *T. reesei* endoglucanase and methods of use thereof.

BACKGROUND

Cellulases are of considerable current interest for converting the cellulosic content of biomass to fermentable sugars for biofuels production. Several enzymes (exoglucanase, endoglucanase, and β-glucosidase) act in concert to hydrolyze cellulose to glucose. The filamentous fungus *Trichoderma reesei* is an industrially used cellulase producer because of its remarkable ability to secrete large quantities of cellulolytic enzymes (>50 g/L). The fungus produces at least seven extracellular cellulases that are required for the complete degradation of crystalline cellulose. These include two exoglucanases, called Cel7A and Cel6A (CBH I and CBH II), that represent 50% and 20% of the total cellulase content, respectively; and five endoglucanases, Cel7B, Cel5A, Cel12A, Cel61A, and Cel45A (EG1, EG2, EG3, EG4, and EG5) that represent 15%, 10%, 1%, <1% and <1% of the total cellulase content, respectively.

Lignocellulose hydrolysis using cellulases at high temperatures has many potential advantages such as higher solid loadings due to reduced viscosity, lower risk of microbial contamination, greater compatibility with high temperature pre-treatments, and faster rates of hydrolysis. However, *T. reesei* cellulases and other fungal enzymes have relatively low activity and stability at higher temperatures (Takashima, S et al., *J Biotechnol* 65(2-3):163-71, 1998). The ability to produce and secrete adequate quantities of cellulases is paramount for the economical production of biofuels from cellulosic biomass, and the expression and production of thermophilic cellulases from non-fungal sources has so far been severely limited (<100 mg/L).

Thus, a need exists in the art for thermostable fungal cellulases that can hydrolyze lignocellulose efficiently at higher temperatures.

BRIEF SUMMARY

Provided are polypeptides, compositions, and methods that meet this need.

The present disclosure relates to mutant thermostable enzymes, including glycosyl hydrolases family 7 enzymes having endoglucanase activity. These enzymes can be used in hydrolyzing lignocellulose, in particular, in degradation and hydrolysis of poly- and oligosaccharides, such as in the conversion into soluble sugars, including for use in the fermentative production of biofuels, processing of food, polishing and cleaning of textiles, production of polished crystalline cellulose and in bleaching of paper pulp. Being thermostable, these enzymes address the need for cellulolytic enzymes able to hydrolyze lignocellulose efficiently at elevated temperatures. The present disclosure also relates to isolated nucleic acids encoding the mutant thermostable enzymes, as well as vectors and host cells containing these nucleic acids.

Accordingly, one aspect of the invention provides a mutant thermostable glycosyl hydrolase family 7 enzyme containing a serine, threonine, leucine, or methionine at an amino acid which aligns with amino acid 230 of SEQ ID NO: 1. In certain embodiments, the enzyme further includes a leucine or serine at an amino acid which aligns with amino acid 113 of SEQ ID NO: 1. In other embodiments, the enzyme further includes a threonine or glycine at an amino acid which aligns with amino acid 115 of SEQ ID NO: 1.

Another aspect of the invention provides a mutant thermostable GH7 family endoglucanase enzyme containing a lysine at an amino acid which aligns with amino acid 230 of SEQ ID NO: 1. In certain embodiments, the enzyme further includes a leucine or serine at an amino acid which aligns with amino acid 113 of SEQ ID NO: 1. In other embodiments, the enzyme further includes a threonine or glycine at an amino acid which aligns with amino acid 115 of SEQ ID NO: 1.

Yet another aspect of the invention provides a mutant thermostable *T. reesei* endoglucanase I enzyme containing an alanine, glutamine, glutamic acid, or arginine at an amino acid which aligns with amino acid 230 of SEQ ID NO: 1. In certain embodiments, the enzyme further includes a leucine or serine at an amino acid which aligns with amino acid 113 of SEQ ID NO: 1. In other embodiments, the enzyme further includes a threonine or glycine at an amino acid which aligns with amino acid 115 of SEQ ID NO: 1.

One aspect of the invention provides a mutant thermostable glycosyl hydrolase family 7 enzyme containing a leucine at an amino acid which aligns with amino acid 113 of SEQ ID NO: 1. In certain embodiments, the mutant thermostable glycosyl hydrolase family 7 enzyme further includes a threonine or glycine at an amino acid which aligns with amino acid 115 of SEQ ID NO: 1.

Another aspect of the invention provides a mutant thermostable GH7 family endoglucanase enzyme containing a serine at an amino acid which aligns with amino acid 113 of SEQ ID NO: 1. In certain embodiments, the mutant thermostable glycosyl hydrolase family 7 enzyme further includes a threonine or glycine at an amino acid which aligns with amino acid 115 of SEQ ID NO: 1.

In embodiments where the mutant thermostable glycosyl hydrolase family 7 enzyme contains a leucine and threonine or glycine at amino acids which align with 113 and 115 of SEQ ID NO: 1 respectively; or where the mutant thermostable GH7 family endoglucanase enzyme contains a serine and threonine or glycine at amino acids which align with 113 and 115 of SEQ ID NO: 1 respectively, the enzyme includes a third mutation of serine, threonine, leucine, methionine, lysine, alanine, glutamine, glutamic acid, or arginine at an amino acid which aligns with amino acid 230 of SEQ ID NO: 1.

Another aspect of the invention provides a mutant thermostable glycosyl hydrolase family 7 enzyme containing a threonine at an amino acid which aligns with amino acid 115 of SEQ ID NO: 1.

Yet another aspect of the invention provides a mutant thermostable *T. reesei* endoglucanase I containing a glycine at an amino acid which aligns with amino acid 115 of SEQ ID NO: 1.

In embodiments which may be combined with any of the preceding aspects in any of their embodiments, the enzyme exhibits increased thermostability as compared to the parent enzyme after incubation at about 50° C. for about one hour. In some embodiments, the enzyme is incubated at 30, 35, 40, 45, 50, 55, 65, or 70° C., for about one hour. In some embodiments, the mutant thermostable enzyme is incubated for 0.5, 0.75, 1.25, 1.5, 1.75, or 2 hours.

In certain embodiments which may be combined with any of the preceding aspects in any of their embodiments, the enzyme has a specific activity of at least about 0.5 mMole GE/µMole enzyme/hr after incubation at about 50° C. for about one hour. In some embodiments, the enzyme has a specific activity of 0.5, 0.6, 0.7, 0.8, 0.9, or 1 mMole GE/µmol enzyme/hour after incubation at about 50° C. for about one hour.

In embodiments which may be combined with any of the preceding aspects providing mutant thermostable glycosyl hydrolase family 7 enzymes in any of their embodiments, the enzyme is an endoglucanase or an exoglucanase.

In embodiments which may be combined with any of the preceding aspects providing mutant thermostable glycosyl hydrolase family 7 enzymes or GH7 family endoglucanase in any of their embodiments, the enzyme is *T. reesei* endoglucanase I. In other embodiments which may be combined with any of the preceding aspects providing mutant thermostable glycosyl hydrolase family 7 enzyme or GH7 family endoglucanase in any of their embodiments, the enzyme is derived from bacteria or from fungi, preferably selected from the group consisting of *Candida, Kluyveromyces, Pichia, Saccharomyces, Schizosaccharomyces, Yarrowia, Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella, Xylaria,* or *Sporotrichum thermophile.*

Another aspect of the invention provides compositions containing the mutant thermostable enzymes according to any of the preceding aspects in any of their embodiments.

Yet another aspect of the invention provides isolated nucleic acids encoding the mutant thermostable enzymes according to the preceding aspects providing the mutant glycosyl hydrolase family 7 enzyme or the GH7 family endoglucanase enzyme or the *T. reesei* endoglucanase I enzyme in any of their embodiments.

One aspect of the invention provides expression vectors containing the nucleic acids of the preceding aspect operably linked to regulatory sequences.

Another aspect of the invention provides host cells containing the expression vectors of the preceding aspect. In certain embodiments, the host cell is selected from the group consisting of *Escherichia, Pseudomonas, Proteus, Ralstonia, Streptomyces, Staphylococcus, Lactococcus, Bacillus, Saccharomyces cerevisiae, Schizosaccharomyces pombe, Yarrowia lipolytica, Hansenula polymorpha, Kluyveromyces lactis, Pichia pastoris, Aspergillus, Chrysosporium lucknowense,* or *Trichoderma reesei.*

Another aspect of the invention provides methods for producing the mutant thermostable enzymes which includes culturing the host cells according to the preceding aspect providing host cells in any of its embodiments in culture medium under conditions suitable to produce the enzymes.

Yet another aspect of the invention provides compositions containing the host cells according to the preceding aspect providing host cells in any of its embodiments and culture medium.

Another aspect of the invention provides compositions containing the mutant thermostable enzyme according to the preceding aspects providing the mutant glycosyl hydrolase family 7 enzyme or the GH7 family endoglucanase enzyme or the *T. reesei* endoglucanase I enzyme in any of their embodiments in the supernatant of the culture medium.

One aspect of the invention provides methods of reducing the viscosity of a pretreated biomass mixture by contacting a pretreated biomass mixture having an initial viscosity with the composition according to the preceding aspects providing compositions; and incubating the contacted biomass mixture under conditions sufficient to reduce the initial viscosity of said pretreated biomass mixture.

Another aspect of the invention provides methods of converting biomass to sugars including contacting biomass with the compositions according to the preceding aspects providing compositions.

Another aspect of the invention provides methods of hydrolyzing or degrading biomass, including contacting the biomass with the compositions according to the preceding aspects providing compositions.

Another aspect of the invention provides methods of producing a fermentation product, including contacting biomass with the compositions according to the preceding aspects providing compositions to form a first product and culturing the first product with one or more fermentative microorganisms under conditions sufficient to produce a fermentation product.

Yet another aspect of the invention provides methods of producing a fermentation product, including contacting biomass with the compositions according to the preceding aspects providing compositions to form a first product and incubating the first product with a chemical solution under conditions sufficient to produce a fermentation product by a chemical process.

One aspect of the invention provides a method of fermenting biomass, including contacting biomass treated by compositions according to the preceding aspects providing compositions with one or more fermentative microorganisms.

Another aspect of the invention provides methods of producing fuels, including contacting biomass with the compositions according to the preceding aspects providing compositions to yield a sugar solution and culturing the sugar solution with a fermentative microorganism under conditions sufficient to produce a fuel.

Yet another aspect of the invention provides methods of producing fuels, including contacting biomass with the compositions according to the preceding aspects providing compositions to yield a sugar solution and incubating the sugar solution with a chemical solution under conditions sufficient to produce a fuel by a chemical process.

In certain embodiments which may be combined with any of the preceding aspects providing methods including contacting biomass, the biomass contains crystalline cellulose. In other embodiments, the biomass contains lignocellulosic plant material. In embodiments where the biomass contains lignocellulosic plant material, the lignocellulosic plant material is selected from *Miscanthus*, energy grass, elephant grass, switchgrass, cord grass, rye grass, reed canary grass, common reed, wheat straw, barley straw, canola straw, oat straw, corn stover, soybean stover, oat hulls, sorghum, rice hulls, sugarcane bagasse, corn fiber, Distillers Dried Grains with Solubles (DDGS), Blue Stem, corncobs, pine, willow, aspen, poplar wood, and energy cane.

One aspect of the invention provides methods of food processing, including contacting biomass with the compositions according to the preceding aspects providing compositions to yield digestible plant material.

Another aspect of the invention provides methods of textile polishing, including contacting textiles with the compositions according to the preceding aspects providing compositions to yield polished textiles.

Yet another aspect of the invention provides methods of textile cleaning, including contacting soiled textiles with the compositions according to the preceding aspects providing compositions to yield clean textiles.

One aspect of the invention provides methods of paper pulp bleaching including contacting paper pulp with the compositions according to the preceding aspects providing compositions to yield bleached paper pulp.

Another aspect of the invention provides methods of producing polished crystalline cellulose, including contacting crystalline cellulose with the compositions according to the preceding aspects providing compositions to yield polished crystalline cellulose.

One aspect of the invention provides laundry detergent compositions containing the mutant thermostable enzymes according to the preceding aspects providing the mutant glycosyl hydrolase family 7 enzyme or the GH7 family endoglucanase enzyme or the *T. reesei* endoglucanase I enzyme in any of their embodiments and detergents.

Another aspect of the invention provides food additives containing the mutant thermostable enzymes according to the preceding aspects providing the mutant glycosyl hydrolase family 7 enzyme or the GH7 family endoglucanase enzyme or the *T. reesei* endoglucanase I enzyme in any of their embodiments.

In certain embodiments which may be combined with any of the preceding aspects providing methods including contacting biomass, plant material, textile, soiled textile, paper pulp, or crystalline cellulose in any of their embodiments, the contacting is conducted at a temperature between about 50° C. and about 55° C., between about 55° C. and about 60° C., or between about 60° C. to about 70° C. In preferred embodiments, the contacting is conducted at a temperature between about 50° C. and about 55° C. In other embodiments, the contacting is conducted at a temperature between about 60° C. and about 70° C. In some embodiments, the biomass, plant material, textile, soiled textile, paper pulp, or crystalline cellulose is pretreated prior to contacting.

DETAILED DESCRIPTION

Figure 1A:
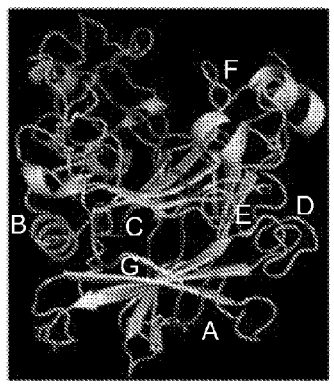
FIG. 1 shows the crystal structure of Endoglucanase I from *Trichoderma reesei*. (a) shows the structure with the mutation sites labeled A-G. (b) shows two views of the structure with the amino acids G230, D113, and D115 labeled. The Protein Data Bank code (PDB) code is 1EG1 (Kleywegt, G J et al., *J Mol Biol* 272(3):383-397, 1997).

The present disclosure relates to mutant thermostable enzymes, including glycosyl hydrolase family 7 enzymes such as endoglucanases, which have mutations at certain amino acid residues. The present disclosure further relates to compositions containing the mutant thermostable enzymes and host cells expressing the enzymes as well as methods for their use.

I. Definitions

Unless defined otherwise, all scientific and technical terms are understood to have the same meaning as commonly used in the art to which they pertain. For the purpose of the present disclosure, the following terms are defined.

The term "amino acid" as used herein refers to a chemical building block of proteins. It includes the 20 standard amino acids commonly found in proteins as well as their chemically-modified versions or analogs.

The term "polypeptide" as used herein refers to a compound made up of a single chain of amino acid residues linked by peptide bonds. The term "protein" is synonymous with the term "polypeptide".

The term "enzyme" as used herein refers to polypeptides which carry out a catalytic function. It can encompass not just the catalytic part of a polypeptide, but also additional domains or motifs that may or may not have functional roles distinct from those of the catalytic domain. These additional domains or motifs can be from other polypeptides found in nature or found commercially.

The term "wild-type" as used herein refers to the non-mutated version of a polypeptide or gene as it appears naturally in a species.

The term "align" as used herein refers to two polypeptides aligning structurally or functionally Amino acids in two or more polypeptides are considered aligned if they are located at the same positions in the different polypeptides. Amino acids in two or more polypeptides are also considered aligned if they perform the same function in the different polypeptides. For instance, aligned amino acids in two or more enzymes could be forming the same contacts, e.g., within each enzyme or with a substrate(s); or performing the same catalytic role during enzyme function. Alignments can be carried out using algorithms well-known in the art.

The term "thermostable" as used herein describes the property of a protein to withstand a limited exposure to certain temperatures, such as high temperatures, without losing the activity it possesses at temperatures where its activity is measurable or is optimal. The term "activity" describes quantitatively the conversion of a given substrate under defined reaction conditions. The term "specific activity" describes quantitatively the activity per amount of enzyme under defined reaction conditions.

The term "cellulase" as used herein refers to an enzyme (or enzymatic activity thereof) that catalyzes an enzymatic reaction in which cellulose is hydrolyzed into glucose, cellobiose, or cellotriose, including enzymes having endoglucanase, exoglucanase, e.g., glucanohydrolase or cellobiohydrolase, β-glucosidase or β-glucosidaseglucohydrolase activity, and the corresponding enzymatic activity of such enzymes.

The term "lignocellulose" as used herein refers to any material primarily consisting of cellulose, hemicellulose, and lignin.

The term "glycosyl hydrolase family 7 enzyme" as used herein refers to enzymes belonging to the glycosyl hydrolase family 7. The term "GH7" is synonymous with glycosyl hydrolase family 7. The term "GH7 family endoglucanase" refers to enzymes in the glycosyl hydrolase family 7 which have endoglucanase function.

II. Mutant Thermostable Enzymes

The present disclosure relates to thermostable enzymes, including enzymes belonging to glycosyl hydrolase family 7, which contain mutations at certain amino acid residues. Applicants do not wish to be bound by any theory; however, it is believed that the increased thermostability is achieved by mutation of residues at flexible sites, which are characterized by high B-factor values during enzyme crystallization. In preferred embodiments, the enzyme is *Trichoderma reesei* endoglucanase I (TrEGI) having mutations at amino acids which align with amino acids 230, 113, or 115 of SEQ ID NO: 1. In other embodiments, the enzyme is a glycosyl hydrolase family 7 (GH7) member having mutations at amino acid positions which align with amino acid 230 and/or 113 and/or 115 of SEQ ID NO: 1. In some embodiments, the GH7 member is an endoglucanase.

Alignment of Amino Acid Sequences

Amino acids of glycosyl hydrolase family 7 members which align with amino acids 230, 113, or 115 of SEQ ID NO: 1 are those which align structurally with amino acids 230, 113, or 115 of SEQ ID NO: 1. The amino acids of glycosyl hydrolase family 7 enzymes which align with amino acids 230, 113, or 115 of SEQ ID NO: 1 may be located at the same position as in SEQ ID NO: 1; more likely, they are not found at the same position as in the reference sequence of SEQ ID NO: 1. For instance, a glycosyl hydrolase family 7 enzyme could have a sequence identical to SEQ ID NO: 1 with an additional methionine at amino acid position 1. In that case, the residue glycine at position 231 of the enzyme would align with amino acid 230 of SEQ ID NO: 1. By way of another example, the amino acid lysine 238 (residue numbering for mature enzyme without signal peptide) of cellobiohydrolase I (CBHI) from *Cochliobolus carbonum* aligns with amino acid 230 of SEQ ID NO:1. The aligned amino acids can be identified, for example, by using algorithms, some of which are discussed below.

Two or more polypeptide sequences can be compared and aligned for maximum correspondence over a comparison window, or designated region as measured using one of the following sequence comparison algorithms or by manual alignment and visual inspection. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. A "comparison window," as used herein, includes reference to a segment of any one of the number of contiguous positions including, but not limited to from 20 to 600, usually about 50 to about 200, more usually about 100 to about 150 in which a sequence may be compared to a reference sequence of the same number of contiguous positions after the two sequences are optimally aligned. Methods of alignment of sequences are well known in the art. An example is using the BLAST algorithm, which is described in Altschul et al. (1997) Nucleic Acids Res 25(17):3389-3402. Other examples for optimal alignment of sequences are the local homology algorithm of Smith and Waterman (1981), the homology alignment algorithm of Needleman and Wunsch (1970) J Mol Biol 48(3):443-453, the search for similarity method of Pearson and Lipman (1988) Proc Natl Acad Sci USA 85(8):2444-2448, computerized implementations of these algorithms (GAP, BESTFIT, FASTA, and TFASTA in the Wisconsin Genetics Software Package, Genetics Computer Group, 575 Science Dr., Madison, Wis.), and manual alignment and visual inspection [see, e.g., Brent et al., (2003) Current Protocols in Molecular Biology, John Wiley & Sons, Inc. (Ringbou Ed)].

More preferably, amino acids which structurally align with other specific amino acids of a reference sequence can be identified by comparison of crystal structures to identify similar structural motifs and flexible regions, the latter characterized by high B-factor values.

Mutations or Substitutions at Amino Acids

The enzyme is composed of an amino acid sequence containing a plurality of consecutive polymerized amino acid residues. Unless otherwise indicated, a particular amino acid sequence also implicitly encompasses conservatively modified variants thereof. Mutant refers to an enzyme in which one or more amino acid residues have been altered from the wild-type sequence by techniques known in the art. Techniques for altering amino acid sequences include, but are not limited to, site-directed mutagenesis, cassette mutagenesis, random mutagenesis, synthetic oligonucleotide construction, cloning and other genetic engineering techniques (Eijsink V G, et al., 2005. Biomol. Eng. 22:21-30). As a result of the alteration in the present disclosure, the mutant enzyme has an increase in thermostability.

A mutant thermostable glycosyl hydrolase family 7 enzyme containing a mutated amino acid residue at an amino acid which aligns with amino acid 230, or 113, or 115 of SEQ ID NO: 1 is one having a mutation in the wild-type amino acid sequence of the enzyme at an amino acid which aligns with amino acid 230, or 113, or 115 of SEQ ID NO: 1. For example, if the wild-type sequence of *T. reesei* endoglucanase I is SEQ ID NO: 1, a mutant *T. reesei* endoglucanase I could have the sequence of SEQ ID NO: 1 with a mutated or substituted amino acid at amino acid 230 or 113 or 115.

In preferred embodiments, the mutant thermostable glycosyl hydrolase family 7 enzyme has amino acid residues, which align with amino acids 230 and/or 113 and/or 115 of SEQ ID NO: 1, substituted/mutated to the residues serine, threonine, leucine, methionine, lysine, alanine, glutamine, glutamic acid, arginine, glycine at an amino acid. In some embodiments, the mutant thermostable glycosyl hydrolase family 7 enzyme is an endoglucanase. Most preferably, the mutant thermostable glycosyl hydrolase family 7 enzyme is *T. reesei* endoglucanase I.

The mutation comprises substitution of amino acids with the naturally-occurring standard 20 amino acid residues, conservatively modified variant amino acid residues, naturally occurring amino acid residues not encoded by a codon, and non-naturally occurring amino acid residues. As a result of the mutation, the enzyme has an increase in thermostability.

"Conservatively modified variant amino acids" as used herein include individual substitutions, deletions or additions to an amino acid sequence which result in the substitution of an amino acid with a chemically similar amino acid. Conservative substitution tables providing functionally similar amino acids are well known in the art. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Glycosyl Hydrolase Family 7 Enzymes

In some embodiments, the mutant thermostable enzyme belongs to the glycosyl hydrolase family 7. Most preferably, the glycosyl hydrolases family 7 enzyme may be an endoglucanase, endo-β-1,4-glucanase, endo-β-1,3-1,4-glucanase, cellobiohydrolase, or exocellulase. In some embodiments, the GH7 enzyme is an endoglucanase. Most preferably, the endoglucanase is a *Trichoderma reesei* endoglucanase I having SEQ ID NO: 1. In some preferred embodiments, the endoglucanase contains a carbohydrate-binding domain (CBM). In other embodiments, the endoglucanase lacks a CBM.

In some embodiments, the enzyme is from bacteria. The bacterial species may be gram positive such as *Bacillus, Streptococcus, Streptomyces, Staphylococcus, Enterococcus, Lactobacillus, Lactococcus, Clostridium, Geobacillus,* or *Oceanobacillus* or gram negative such as *Escherichia coli, Pseudomonas, Salmonella, Campylobacter, Helicobacter, Flavobacterium, Fusobacterium, Ilyobacter, Neissena,* or *Ureaplasma*. In some preferred embodiments, the enzyme is from *Bacillus alkalophilus, Bacillus amyloliquefaciens, Bacillus brevis, Bacillus circulans, Bacillus clausii, Bacillus coagulans, Bacillus formus, Bacillus lautus, Bacillus lentus, Bacillus licheniformis, Bacillus megaterium, Bacillus pumilus, Bacillus stearothermophilus, Bacillus subtilis,* or *Bacillus thuringiensis*. In other embodiments, the enzyme is from *Streptococcus equisimilis, Streptococcus pyogenes, Streptococcus uberis, Streptococcus equi* subsp. *Zooepidemicus, Streptomyces achromogenes, Streptomyces avermitilis, Streptomyces coelicolor, Streptomyces griseus,* or *Streptomyces lividans*.

In some embodiments, the enzyme is from fungi. In preferred embodiments, the enzyme is from yeast species including *Candida, Kluyveromyces, Pichia, Saccharomyces, Schizosaccharomyces,* or *Yarrowia* or from filamentous fungal species including *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella, Xylaria,* or *Sporotrichum thermophile*. In some embodiments, the enzyme is from *Saccharomyces carlsbergensis, Saccharomyces cerevisiae, Saccharomyces diastaticus, Saccharomyces douglasii, Saccharomyces kluyveri, Saccharomyces norbensis,* or *Saccharomyces oviformis*. In other embodiments, the enzyme is from *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chry-* sosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Trichoderma harzianum, Trichoderma koningii, Trichoderma longibrachiatum, Trichoderma reesei, or Trichoderma viride. In preferred embodiments, the enzyme is from Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, or Thielavia terrestris.

Enzyme Thermostability/Activity

The activity of an enzyme can be used as measure of its thermostability. Monitoring enzymatic activity under different reaction conditions, e.g., at different temperatures, translates to monitoring the stability of the enzyme under those conditions. If the enzyme is active under certain reaction conditions, it is considered stable under those conditions.

In preferred embodiments, the mutant thermostable enzymes exhibit increased activity/thermostability as compared to the parent, non-mutated wild type enzyme after incubation at temperatures of about 30, 35, 40, 45, 50, 55, 65, or 70° C., for about one hour. In some embodiments, the mutant thermostable enzyme is incubated for 0.5, 0.75, 1.25, 1.5, 1.75, or 2 hours.

In some preferred embodiments, the mutant thermostable enzyme has a specific activity of at least about 0.5, typically at least about 0.5, 0.6, 0.7, 0.8, 0.9, or 1 mMole GE/µmol enzyme/hour after incubation at about 50° C. for about one hour. The enzyme generally has cellulase activity, for example, endoglucanase, exoglucanase, cellobiohydrolase, and/or cellulose-binding ability.

Cellulase activity or cellulose-binding ability can be measured by a number of well-known methods, including zymograms, reducing sugar assays (e.g., DNS Micro or Macro, Nelson-Somogyi Micro or Macro, Nelson Semi-Micro, Ferricyanide-1, Ferricyanide-2, PAHBAH Micro or Macro, BCA, and Modified BCA), assays using paranitrophenol-labeled glycosides, product analysis, total sugar assays, such as Phenol-$H_2SO_4$ or Anthrone $H_2SO_4$, enzymatic glucose assays, and cellulose binding assays.

Substrates for cellulase activity and cellulose-binding ability include soluble and insoluble substrates. Soluble substrates include, for example, cellodextrins and their derivatives, including radiolabelled versions thereof, short chain cellulase, β-methylumbelliferyl-oligosaccharides, p-nitrophenol-oligosaccharides, Long chain cellulose derivatives, Carboxymethyl cellulose (CMC), hydroxyethyl cellulose (HEC), dyed CMC. Insoluble substrates, include, for example, cotton, Whatman No. 1 filter paper, pulp (e.g., Solka Floc), crystalline cellulose, such as cotton, microcrystalline cellulose (e.g., Avicel®), valonia cellulose, bacterial cellulose, amorphous cellulose (e.g., PASC, alkali-swollen cellulose), dyed cellulose, fluorescent cellulose, chromogenic and fluorephoric derivatives, such as trinitrophenyl-carboxymethylcellulose (TNP-CMC) and fluram-cellulose, practical cellulose-containing substrates, α-cellulose, and pretreated lignocellulosic biomass.

Mutation at Amino Acid 230

In one aspect, the present disclosure relates to mutant thermostable glycosyl hydrolase family 7 enzymes having a mutation at an amino acid which aligns with amino acid 230 of SEQ ID NO: 1.

In preferred embodiments, the mutant thermostable glycosyl hydrolases family 7 enzyme has a serine, threonine, leucine, or methionine at an amino acid which aligns with amino acid 230 of SEQ ID NO: 1.

In another preferred embodiment, the mutant thermostable glycosyl hydrolases family 7 enzyme is a GH7 family endoglucanase enzyme having a lysine at an amino acid which aligns with amino acid 230 of SEQ ID NO: 1.

In another preferred embodiment, the mutant thermostable glycosyl hydrolases family 7 enzyme is a T. reesei endoglucanase I enzyme having an alanine, glutamine, glutamic acid, or arginine at an amino acid which aligns with amino acid 230 of SEQ ID NO: 1.

Mutation at Amino Acid 113

In another aspect, the present disclosure relates to mutant thermostable glycosyl hydrolases family 7 enzymes having a mutation at an amino acid which aligns with amino acid 113 of SEQ ID NO: 1.

In preferred embodiments, the mutant thermostable glycosyl hydrolases family 7 enzyme has a leucine at an amino acid which aligns with amino acid 113 of SEQ ID NO: 1.

In another preferred embodiment, the mutant thermostable glycosyl hydrolases family 7 enzyme is a GH7 family endoglucanase enzyme having a serine at an amino acid which aligns with amino acid 113 of SEQ ID NO: 1.

Mutation at Amino Acid 115

In yet another aspect, the present disclosure relates to mutant thermostable glycosyl hydrolases family 7 enzymes having a mutation at an amino acid which aligns with amino acid 115 of SEQ ID NO: 1.

In preferred embodiments, the mutant thermostable glycosyl hydrolases family 7 enzyme has a threonine at an amino acid which aligns with amino acid 115 of SEQ ID NO: 1.

In another preferred embodiment, the mutant thermostable glycosyl hydrolases family 7 enzyme is a T. reesei endoglucanase I enzyme having a glycine at an amino acid which aligns with amino acid 115 of SEQ ID NO: 1.

Enzymes Containing Combination of Mutations

The present disclosure relates to mutant thermostable enzymes, including glycosyl hydrolase family 7 enzymes, having mutations at certain amino acids. In preferred embodiments, the mutant thermostable glycosyl hydrolase family 7 enzyme has a mutation at an amino acid which aligns with amino acid 230 or 113 or 115 of SEQ ID NO: 1. In some embodiments, the mutant thermostable glycosyl hydrolase family 7 enzyme has combinations of the mutations at amino acids which align with amino acid 230, 113, or 115. For example, the mutant thermostable glycosyl hydrolase family 7 enzyme could have a mutation at the amino acid which aligns with amino acid 230 of SEQ ID NO: 1 and a mutation at the amino acid which aligns with amino acid 113 of SEQ ID NO: 1. The present disclosure includes mutant thermostable glycosyl hydrolase family 7 enzymes having all possible combinations of the mutations at amino acids which align with amino acid 230, 113, or 115, as described above.

A) Mutations at Amino Acids 113 and 115

In one aspect, the present disclosure relates to mutant thermostable glycosyl hydrolases family 7 enzyme having a mutation at an amino acid which aligns with amino acid 113 of SEQ ID NO: 1 and a further mutation at a second amino acid which aligns with amino acid 115 of SEQ ID NO: 1.

In preferred embodiments, the mutant thermostable glycosyl hydrolases family 7 enzyme has a leucine at an amino acid which aligns with amino acid 113 of SEQ ID NO: 1 and a further mutation at a second amino acid which aligns with amino acid 115 of SEQ ID NO: 1.

In preferred embodiments, the mutant thermostable glycosyl hydrolases family 7 enzyme has a leucine at an amino acid which aligns with amino acid 113 of SEQ ID NO: 1 and a threonine or a glycine at a second amino acid which aligns with amino acid 115 of SEQ ID NO: 1.

In another preferred embodiment, the mutant thermostable glycosyl hydrolases family 7 enzyme is a GH7 family endoglucanase enzyme having a mutation at an amino acid which aligns with amino acid 113 of SEQ ID NO: 1 and a further mutation at a second amino acid which aligns with amino acid 115 of SEQ ID NO: 1.

In another preferred embodiment, the mutant thermostable glycosyl hydrolases family 7 enzyme is a GH7 family endoglucanase enzyme having a serine at an amino acid which aligns with amino acid 113 of SEQ ID NO: 1 and a threonine or a glycine at a second amino acid which aligns with amino acid 115 of SEQ ID NO: 1.

B) Mutations at Amino Acids 113, 115, and 230

In preferred embodiments, the mutant thermostable glycosyl hydrolase family 7 enzyme with a leucine at an amino acid which aligns with amino acid 113 of SEQ ID NO: 1 and a threonine or a glycine at a second amino acid which aligns with amino acid 115 of SEQ ID NO: 1 has a further mutation at an amino acid which aligns with amino acid 230 of SEQ ID NO: 1.

In preferred embodiments, the mutant thermostable glycosyl family hydrolase family 7 enzyme with a leucine at an amino acid which aligns with amino acid 113 of SEQ ID NO: 1 and a threonine or a glycine at a second amino acid which aligns with amino acid 115 of SEQ ID NO: 1 has a serine, threonine, leucine, methionine, lysine, alanine, glutamine, glutamic acid, or arginine at an amino acid which aligns with amino acid 230 of SEQ ID NO: 1.

In another preferred embodiment, the mutant thermostable glycosyl hydrolases family 7 enzyme is a GH7 family endoglucanase enzyme with a serine at an amino acid which aligns with amino acid 113 of SEQ ID NO: 1 and a threonine or a glycine at a second amino acid which aligns with amino acid 115 of SEQ ID NO: 1 has a further mutation at an amino acid which aligns with amino acid 230 of SEQ ID NO: 1.

In another preferred embodiment, the mutant thermostable glycosyl hydrolases family 7 enzyme is a GH7 family endoglucanase enzyme with a serine at an amino acid which aligns with amino acid 113 of SEQ ID NO: 1 and a threonine or a glycine at a second amino acid which aligns with amino acid 115 of SEQ ID NO: 1 has a serine, threonine, leucine, methionine, lysine, alanine, glutamine, glutamic acid, or arginine at an amino acid which aligns with amino acid 230 of SEQ ID NO: 1.

C) Mutations at Amino Acids 230 and 113

In one aspect, the mutant thermostable glycosyl hydrolases family 7 enzyme having a mutation at an amino acid which aligns with amino acid 230 of SEQ ID NO: 1 has a further mutation at an amino acid which aligns with amino acid 113 of SEQ ID NO: 1.

In preferred embodiments, the mutant thermostable glycosyl hydrolases family 7 enzyme having a serine, threonine, leucine, or methionine at an amino acid which aligns with amino acid 230 of SEQ ID NO: 1 has a further mutation at an amino acid which aligns with amino acid 113 of SEQ ID NO: 1.

In other preferred embodiments, the mutant thermostable glycosyl hydrolases family 7 enzyme having a serine, threonine, leucine, or methionine at an amino acid which aligns with amino acid 230 of SEQ ID NO: 1 has a leucine or serine at an amino acid which aligns with amino acid 113 of SEQ ID NO: 1.

In preferred embodiments, the mutant thermostable glycosyl hydrolases family 7 enzyme is a GH7 family endoglucanase enzyme with a mutation at an amino acid which aligns with amino acid 230 of SEQ ID NO: 1 has a further mutation at an amino acid which aligns with amino acid 113 of SEQ ID NO: 1.

In other preferred embodiments, the mutant thermostable glycosyl hydrolases family 7 enzyme is a GH7 family endoglucanase enzyme with a lysine at an amino acid which aligns with amino acid 230 of SEQ ID NO: 1 has a further mutation at an amino acid which aligns with amino acid 113 of SEQ ID NO: 1.

In preferred embodiments, the mutant thermostable glycosyl hydrolases family 7 enzyme is a GH7 family endoglucanase enzyme with a lysine at an amino acid which aligns with amino acid 230 of SEQ ID NO: 1 has a leucine or serine at an amino acid which aligns with amino acid 113 of SEQ ID NO: 1.

In preferred embodiments, the mutant thermostable glycosyl hydrolases family 7 enzyme is a *T. reesei* endoglucanase I enzyme having a mutation at an amino acid which aligns with amino acid 230 of SEQ ID NO: 1 has a further mutation at an amino acid which aligns with amino acid 113 of SEQ ID NO: 1.

In another preferred embodiment, the mutant thermostable glycosyl hydrolases family 7 enzyme is a *T. reesei* endoglucanase I enzyme having an alanine, glutamine, glutamic acid, or arginine at an amino acid which aligns with amino acid 230 of SEQ ID NO: 1 has a further mutation at an amino acid which aligns with amino acid 113 of SEQ ID NO:1.

In another preferred embodiment, the mutant thermostable glycosyl hydrolases family 7 enzyme is a *T. reesei* endoglucanase I enzyme having an alanine, glutamine, glutamic acid, or arginine at an amino acid which aligns with amino acid 230 of SEQ ID NO: 1 has leucine or serine at an amino acid which aligns with amino acid 113 of SEQ ID NO: 1.

D) Mutations at Amino Acids 230 and 115.

In one aspect, the mutant thermostable glycosyl hydrolases family 7 enzyme having a mutation at an amino acid which aligns with amino acid 230 of SEQ ID NO: 1 has a further mutation at an amino acid which aligns with amino acid 115 of SEQ ID NO: 1.

In preferred embodiments, the mutant thermostable glycosyl hydrolases family 7 enzyme having a serine, threonine, leucine, or methionine at an amino acid which aligns with amino acid 230 of SEQ ID NO: 1 has a further mutation at an amino acid which aligns with amino acid 115 of SEQ ID NO: 1.

In other preferred embodiments, the mutant thermostable glycosyl hydrolases family 7 enzyme having a serine, threonine, leucine, or methionine at an amino acid which aligns with amino acid 230 of SEQ ID NO: 1 has a threonine or glycine at an amino acid which aligns with amino acid 115 of SEQ ID NO: 1.

In preferred embodiments, the mutant thermostable glycosyl hydrolases family 7 enzyme is a GH7 family endoglucanase enzyme with a mutation at an amino acid which aligns with amino acid 230 of SEQ ID NO: 1 has a further mutation at an amino acid which aligns with amino acid 115 of SEQ ID NO: 1.

In other preferred embodiments, the mutant thermostable glycosyl hydrolases family 7 enzyme is a GH7 family endoglucanase enzyme with a lysine at an amino acid which aligns with amino acid 230 of SEQ ID NO: 1 has a further mutation at an amino acid which aligns with amino acid 115 of SEQ ID NO: 1.

In preferred embodiments, the mutant thermostable glycosyl hydrolases family 7 enzyme is a GH7 family endoglucanase enzyme with a lysine at an amino acid which aligns with amino acid 230 of SEQ ID NO: 1 has a threonine or glycine at an amino acid which aligns with amino acid 115 of SEQ ID NO: 1.

In preferred embodiments, the mutant thermostable glycosyl hydrolases family 7 enzyme is a *T. reesei* endoglucanase I enzyme having a mutation at an amino acid which aligns with amino acid 230 of SEQ ID NO: 1 has a further mutation at an amino acid which aligns with amino acid 115 of SEQ ID NO: 1.

In another preferred embodiment, the mutant thermostable glycosyl hydrolases family 7 enzyme is a *T. reesei* endoglucanase I enzyme having an alanine, glutamine, glutamic acid, or arginine at an amino acid which aligns with amino acid 230 of SEQ ID NO: 1 has a further mutation at an amino acid which aligns with amino acid 115 of SEQ ID NO: 1.

In another preferred embodiment, the mutant thermostable glycosyl hydrolases family 7 enzyme is a *T. reesei* endoglucanase I enzyme having an alanine, glutamine, glutamic acid, or arginine at an amino acid which aligns with amino acid 230 of SEQ ID NO: 1 has a threonine or glycine at an amino acid which aligns with amino acid 115 of SEQ ID NO: 1.

III. Polypeptides Comprising Mutant Thermostable Enzymes

In some embodiments, the provided enzyme is fused to a functional domain including a leader peptide, propeptide, binding domain and/or catalytic domain. Suitable binding domains include, but are not limited to, carbohydrate-binding domains (e.g., CBM) of various specificities, providing increased affinity to carbohydrate components present during the application of the mutant thermostable enzyme. Suitable enzymatically active domains possess an activity that supports the action of the mutant thermostable enzyme in producing the desired product. Non-limiting examples of catalytic domains include: cellulases, hemicellulases such as xylanase, endo-mannanases, exo-mannanases, glucanases, arabinases, galactosidases, pectinases, and/or other activities such as proteases, lipases, acid phosphatases and/or others or functional fragments thereof.

Fusion proteins are optionally linked to the polypeptide through a linker sequence that simply joins the provided mutant thermostable enzyme or fragment thereof and the fusion domain without significantly affecting the properties of either component, or the linker optionally has a functional importance for the intended application. In some embodiments, a proteolytic cleavage site is provided between the fusion protein partner and the protein sequence of interest to allow removal of fusion protein sequences.

IV. Nucleic Acids, Vectors and Host Cells

Also provided are vectors, host cells, and methods for the production of the mutant thermostable enzymes. In one aspect, the present disclosure provides isolated nucleic acids encoding the mutant thermostable enzymes. In another aspect, the present disclosure provides expression vectors containing isolated nucleic acids encoding the mutant thermostable enzymes. In yet another aspect, the present disclosure provides host cells having expression vectors containing isolated nucleic acids encoding the mutant thermostable enzymes. In another aspect, the present disclosure provides a method of producing the mutant thermostable enzymes by culturing host cells containing expression vectors having nucleic acids encoding the mutant thermostable enzymes under conditions suitable for enzyme production.

In some embodiments, the DNA encoding the enzyme can be chemically synthesized from published sequences or obtained directly from host cells harboring the gene (e.g., by cDNA library screening or PCR amplification). In some embodiments, the enzyme is included in an expression cassette and/or cloned into a suitable expression vector by standard molecular cloning techniques. Such expression cassettes or vectors contain sequences that assist initiation and termination of transcription (e.g., promoters and terminators), and generally contain a selectable marker.

Expression vector/host cell combinations are well-known and can be used in the provided methods. Typically, the expression cassette or vector is introduced in a suitable expression host cell, which then expresses the corresponding polypeptide. Particularly suitable expression hosts are bacterial expression host genera including *Escherichia* (e.g., *Escherichia coli*), *Pseudomonas* (e.g., *P. fluorescens* or *P. stutzerei*), *Proteus* (e.g., *Proteus mirabilis*), *Ralstonia* (e.g., *Ralstonia eutropha*), *Streptomyces*, *Staphylococcus* (e.g., *S. carnosus*), *Lactococcus* (e.g., *L. lactis*), or *Bacillus* (*subtilis*, *megaterium*, *licheniformis*, etc.). Also particularly suitable are yeast expression hosts such as *Saccharomyces cerevisiae*, *Schizosaccharomyces pombe*, *Yarrowia lipolytica*, *Hansenula polymorpha*, *Kluyveromyces lactis* or *Pichia pastoris*. Especially suited are fungal expression hosts such as *Aspergillus niger*, *Chrysosporium lucknowense*, *Aspergillus* (e.g., *A. oryzae*, *A. niger*, *A. nidulans*, etc.) or *Trichoderma reesei*. Also suited are mammalian expression hosts such as mouse (e.g., NS0), Chinese Hamster Ovary (CHO) or Baby Hamster Kidney (BHK) cell lines. Other eukaryotic hosts such as insect cells or viral expression systems (e.g., bacteriophages such as M13, T7 phage or Lambda, or viruses such as Baculovirus) are also suitable for producing the mutant thermostable enzymes.

Promoters and/or signal sequences associated with secreted proteins in a particular host of interest are candidates for use in the heterologous production and secretion of the enzymes in that host or in other hosts. As an example, in filamentous fungal systems, the promoters that drive the genes for cellobiohydrolase I (cbh1), glucoamylase A (glaA), TAKA-amylase (amyA), xylanase (exlA), the gpd-promoter cbh1, cbh11, endoglucanase genes EGI-EGV, Cel61B, Cel74A, eg11-eg15, gpd promoter, Pgk1, pki1, EF-1alpha, tef1, cDNA1 and hex1 are particularly suitable and can be derived from a number of different organisms (e.g., *A. niger, T. reesei, A. oryzae, A. awamori,* and *A. nidulans*). In some embodiments, the enzyme is recombinantly associated with a polynucleotide encoding a suitable homologous or heterologous signal sequence that leads to secretion of the mutant thermostable enzyme into the extracellular (or periplasmic) space, thereby allowing direct detection of enzyme activity in the cell supernatant (or periplasmic space or lysate). Particularly suitable signal sequences for *Escherichia coli*, other Gram negative bacteria and other organisms known in the art include those that drive expression of the HlyA, DsbA, Pbp, PhoA, PelB, OmpA, OmpT or M13 phage Gill genes. For *Bacillus subtilis*, Gram-positive organisms and other organisms known in the art, particularly suitable signal sequences further include those that drive expression of the AprE, NprB, Mpr, AmyA, AmyE, Blac, SacB, and for *S. cerevisiae* or other yeast, include the killer toxin, Bar1, Suc2, Mating factor α, Inu1A or Ggplp signal sequence. Signal sequences can be cleaved by a number of signal peptidases, thus removing them from the rest of the expressed protein. In some embodiments, the rest of the enzyme is expressed alone or as a fusion with other peptides, tags or proteins located at the N- or C-terminus (e.g., 6XHis, HA or FLAG tags). Suitable fusions include tags, peptides or proteins that facilitate affinity purification or detection (e.g., 6XHis, HA, chitin binding protein, thioredoxin or FLAG tags), as well as those that facilitate expression, secretion or processing of the provided polypeptide. Suitable processing sites include enterokinase, STE13, Kex2 or other protease cleavage sites for cleavage in vivo or in vitro.

In some embodiments, the enzymes are introduced into expression host cells by a number of transformation methods including, but not limited to, electroporation, lipid-assisted transformation or transfection ("lipofection"), chemically mediated transfection (e.g., using calcium chloride and/or calcium phosphate), lithium acetate-mediated transformation (e.g., of host-cell protoplasts), biolistic "gene gun" transformation, PEG-mediated transformation (e.g., of host-cell protoplasts), protoplast fusion (e.g., using bacterial or eukaryotic protoplasts), liposome-mediated transformation, *Agrobacterium tumefaciens*, adenovirus or other viral or phage transformation or transduction.

Alternatively, the enzymes are expressed intracellularly. Optionally, after intracellular expression of the enzymes or secretion into the periplasmic space using signal sequences such as those mentioned above, a permeabilisation or lysis step can be used to release the mutant thermostable enzyme into the supernatant. The disruption of the membrane barrier is effected by the use of mechanical means such as ultrasonic waves, pressure treatment (French press), cavitation or the use of membrane-digesting enzymes such as lysozyme or enzyme mixtures. As a further alternative, the polynucleotides encoding the enzyme are expressed by use of a suitable cell-free expression system. In cell-free systems, the polynucleotide of interest is typically transcribed with the assistance of a promoter, but ligation to form a circular expression vector is optional. In other embodiments, RNA is exogenously added or generated without transcription and translated in cell-free systems.

In some embodiments, the enzymes are produced recombinantly, while in others the polypeptides are produced synthetically, or are purified from a native source.

In some embodiments, the enzymes are produced as N- and/or C-terminal fusion proteins, for example to aid in extraction, detection and/or purification. Examples of fusion protein partners include, but are not limited to, glutathione-S-transferase (GST), 6XHis, GAL4 (DNA binding and/or transcriptional activation domains), FLAG-, MYC-tags or other tags well known to anyone skilled in the art. In some embodiments, a proteolytic cleavage site is provided between the fusion protein partner and the protein sequence of interest to allow removal of fusion protein sequences. Preferably, the fusion protein does not hinder the activity of the provided polypeptide.

V. Compositions

In some aspects, the present disclosure provides compositions containing mutant thermostable glycosyl hydrolases family 7 enzymes having mutations at certain amino acid residues. In some embodiments, the disclosure provides compositions containing host cells containing expression vectors having nucleic acids encoding mutant thermostable glycosyl hydrolases family 7 enzymes. In other embodiments, the disclosure provides compositions containing mutant thermostable glycosyl hydrolases family 7 enzymes in the supernatant of culture media. In preferred embodiments, the mutant thermostable glycosyl hydrolases family 7 enzyme is a GH7 family endoglucanase. In another preferred embodiment, the mutant thermostable glycosyl hydrolases family 7 enzyme is *T. reesei* endoglucanase I.

In some embodiments, the compositions include one or more additional proteins of interest. Non-limiting examples of proteins of interest which may be found in the composition include: hemicellulases, alpha-galactosidases, beta-galactosidases, lactases, beta-glucanases, endo-beta-1,4-glucanases, cellulases, xylosidases, xylanases, xyloglucanases, xylan acetyl-esterases, galactanases, endo-mannanases, exo-mannanases, pectinases, pectin lyases, pectinesterases, polygalacturonases, arabinases, rhamnogalacturonases, laccases, reductases, oxidases, phenoloxidases, ligninases, proteases, amylases, phosphatases, lipolytic enzymes, cutinases and/or other enzymes.

VI. METHODS FOR USE

The enzymes, vectors, host cells, and compositions of the present disclosure find use in a variety of industrial applications, including in the degradation of biomass, e.g., cellulose and lignocellulose, into monosaccharides and oligosaccharides, for example, in biofuel production, textile methods, including cleaning, cotton softening, and denim finishing, in production and uses of detergents, for example, for color care, cleaning, and anti-deposition; for food-based methods, including food processing and mashing; for pulp and paper methods, such as paper pulp bleaching, deinking, drainage improvement, production of polished crystalline cellulose, and fiber modification. Thus, also provided are methods and uses of the provided enzymes, nucleic acid, and compositions for such purposes, for example, in degrading or hydrolyzing cellulose-containing compositions to produce soluble sugars, for example, followed by enzymatic or chemical fermentation.

The mutant thermostable enzymes retain enzyme activity at high temperatures. In some embodiments, the mutant thermostable enzymes are used at temperatures between about 50 and 55° C., typically about 50, 51, 52, 53, or 54° C.; between about 55 and 60° C., typically about 55, 56, 57, 58, or 59° C.; or between about 60 and 70° C., typically about 60, 61, 62, 63, 64, 65, 66, 67, 68, 69, or 70° C.

This increased thermostability makes the mutant enzymes particularly suitable for lignocellulose hydrolysis, which is ideally carried out at elevated temperatures. Because of this property, the mutant thermostable enzymes can be used in the various industrial applications discussed below.

Reduction of the Viscosity of Pretreated Biomass Mixtures

The provided compositions containing mutant thermostable enzymes, host cells expressing the mutant thermostable enzymes, or the mutant thermostable enzymes in the supernatant of culture media find use in a variety of industrial applications, including in the reduction of the viscosity of pretreated biomass mixtures prior to their degradation into monosaccharides and oligosaccharides, for example, in biofuel production.

Biomass that is used as a feedstock, for example, in biofuel production, generally contains high levels of lignin, which can block hydrolysis of the cellulosic component of the biomass. Typically, biomass is pretreated with, for example, high temperature and/or high pressure to increase the accessibility of the cellulosic component to hydrolysis. However, pretreatment generally results in a biomass mixture that is highly viscous. The high viscosity of the pretreated biomass mixture can also interfere with effective hydrolysis of the pretreated biomass. Advantageously, the polypeptides and compositions of the present disclosure can be used to reduce the viscosity of pretreated biomass mixtures prior to further degradation of the biomass.

Accordingly, certain embodiments of the present disclosure relate to methods of reducing the viscosity of a pretreated biomass mixture, by contacting a pretreated biomass mixture having an initial viscosity with any of the compositions containing mutant thermostable enzymes, host cells expressing the mutant thermostable enzymes, or the mutant thermostable enzymes in the supernatant of culture media of the present disclosure; and incubating the contacted biomass mixture under conditions sufficient to reduce the initial viscosity of the pretreated biomass mixture.

In some embodiments, the disclosed methods are carried out as part of a pretreatment process. The pretreatment process may include the additional step of adding any of the compositions containing mutant thermostable enzymes, host cells expressing the mutant thermostable enzymes, or the mutant thermostable enzymes in the supernatant of culture media of the present disclosure to pretreated biomass mixtures after the step of pretreating the biomass under high temperature, and incubating the pretreated biomass with the compositions containing mutant thermostable enzymes, host cells expressing the mutant thermostable enzymes, or the mutant thermostable enzymes in the supernatant of culture media under conditions sufficient to reduce the viscosity of the mixture. The compositions containing mutant thermostable enzymes, host cells expressing the mutant thermostable enzymes, or the mutant thermostable enzymes in the supernatant of culture media may be added to the pretreated biomass mixture while the temperature of the mixture is high, or after the temperature of the mixture has decreased. In some embodiments, the methods are carried out in the same vessel or container where the heat pretreatment was performed. In other embodiments, the methods are carried out in a separate vessel or container where the heat pretreatment was performed.

Biomass can include, but is not limited to, plant material, municipal solid waste, and wastepaper. Plant material includes but is not limited to *Miscanthus*, energy grass, elephant grass, switchgrass, cord grass, rye grass, reed canary grass, common reed, wheat straw, barley straw, canola straw, oat straw, corn stover, soybean stover, oat hulls, oat spelt, sorghum, rice hulls, sugarcane bagasse, corn fiber, barley, oats, flax, wheat, linseed, citrus pulp, cottonseed, groundnut, rapeseed, sunflower, peas, lupines, palm kernel, coconut, konjac, locust bean gum, gum guar, soy beans, Distillers Dried Grains with Solubles (DDGS), Blue Stem, corncobs, pine, conifer softwood, eucalyptus, birchwood, willow, aspen, poplar wood, hybrid poplar, energy cane, short-rotation woody crop, crop residue, yard waste, or a combination thereof.

Degradation of Biomass

The provided compositions containing mutant thermostable enzymes, host cells expressing the mutant thermostable enzymes, or the mutant thermostable enzymes in the supernatant of culture media may be used to degrade various types of cellulosic biomass, which are well-known in the art, including plant biomass, microbial biomass, purified cellulose, and lignocellulosic feedstocks.

Bioenergy feedstocks consist primarily of the plant cell wall components cellulose and hemicellulose. Hydrolysis of these polysaccharides to their monomeric sugars involves a set of enzymes acting synergistically to cleave the different chemical linkages (Dodd and Cann, GCB Bioenergy, 1:2, 2009). Cellulose is the predominant polysaccharide in biomass (with others including hemicellulose, lignin, and pectin). It is a homopolymer of anhydrocellobiose (a linear β-(1-4)-D-glucan), and includes glucose units linked together in β-1, 4-glycosidic linkages. The hemicellulosic component can vary in chemical composition. Hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains.

Cellulosic biomass includes lignocellulose biomass, containing cellulose, hemicellulose, and lignin. Purified celluloses include holocellulases, such as Solka Flok, microcrystalline celluloses, such as Avicel® and Sigmacell®, and the highly soluble cellulose ether, carboxymethylcellulose (CMC). Cellulose-containing substrates include soluble and substrates, such as cellodextrins and their derivatives, short chain cellulase, β-methylumbelliferyl-oligosaccharides, p-nitrophenol-oligosaccharides, long chain cellulose derivatives, carboxymethyl cellulose (CMC), hydroxyethyl cellulose (HEC), and insoluble substrates, including cotton, Whatman No. 1 filter paper, Pulp (e.g., Solka Floc), crystalline cellulose, such as cotton, microcrystalline cellulose (e.g., Avicel®), Valonia cellulose, bacterial cellulose, amorphous cellulose (e.g., PASC, alkali-swollen cellulose), dyed cellulose, fluorescent cellulose, chromogenic and fluorephoric derivatives, such as trinitrophenyl-carboxymethylcellulose (TNP-CMC) and Fluram-cellulose, practical cellulose-containing substrates, α-cellulose, and pre-treated lignocellulosic biomass.

In some aspects, the compositions containing mutant thermostable enzymes, host cells expressing the mutant thermostable enzymes, or the mutant thermostable enzymes in the supernatant of culture media are used to contact crystalline cellulose to yield polished crystalline cellulose which can be used for assays of cellulases, expansins, and cellulose-binding proteins.

In other aspects, the compositions containing mutant thermostable enzymes, host cells expressing the mutant thermostable enzymes, or the mutant thermostable enzymes in the supernatant of culture media are used to contact biomass to hydrolyze/degrade it or convert it to sugars. In some embodiments, the compositions containing mutant thermostable enzymes, host cells expressing the mutant thermostable enzymes, or the mutant thermostable enzymes in the supernatant of culture media are used to contact biomass and the product is cultured with fermentative microorganism(s) or incubated with a chemical solution under conditions sufficient to produce a fermentative product. In other embodiments, biomass is treated by the compositions containing mutant thermostable enzymes, host cells expressing the mutant thermostable enzymes, or the mutant thermostable enzymes in the supernatant of culture media, and contacted with one or more fermentative microorganisms to ferment the biomass. In preferred embodiments, the biomass is pretreated.

Biofuel Production

The provided enzymes and compositions of the present disclosure find use in the degradation and hydrolysis of cellulose and cellulose-containing biomass and feedstocks, for example, for the production of monosaccharides, disaccharides, and oligosaccharides as chemical or fermentation feedstocks from biomass for the production of biofuel, such as ethanol, butanol, other products, or intermediates. Provided are methods and compositions for such uses of the provided polypeptides, such as conversion of lignocellulolytic biomass into soluble sugars for fermentative production of biofuels, conversion of pre-treated lignocellulose into soluble sugars, conversion of lignocellulose into soluble sugars in the presence of high salt or ionic liquids, conversion of crystalline cellulose into soluble sugars at high temperatures, such as 50, 51, 52, 53, 54, or 55° C., or over a range, e.g., between 60° C. and 70° C.

In one embodiment, the provided composition includes the enzyme in a composition of crude fermentation broth with or without the cells removed or in the form of a semi-purified or purified enzyme preparation. Alternatively, the provided host cells of the present disclosure are used as a source of polypeptide in a fermentation process with the biomass.

In one embodiment, the enzymes of the present disclosure find use in the degradation of cellulose to aid in the degradation of biomass, to form biofuels, such as ethanol. Ethanol is produced by enzymatic degradation of biomass and conversion of the released saccharides to ethanol. This kind of ethanol is often referred to as bioethanol or biofuel. It is used as a fuel additive or extender in blends of from less than 1% and up to 100% (a fuel substitute). In one embodiment, for the production of biofuels from biomass, the provided enzymes, compositions, and methods are used in the conversion of cellulose to its monomer (glucose) or other soluble sugar for subsequent conversion to biofuel (e.g., ethanol) by fermentation, such as by microbial or chemical fermentation. For example, the provided enzymes and methods may be used for such conversion by enzymatic hydrolysis, optionally including acid pre-treatment, typically carried out at high temperatures, followed by hydrolysis with the provided polypeptides.

In one embodiment, the provided enzymes are used in combination with other carbohydrases (e.g., mannanases, glucanase, xylanase, alpha-galactosidase and/or cellulase) for more extensive hydrolysis of the plant material.

Food Processing

Compositions comprising the enzymes of the present disclosure also find use in the processing and manufacturing of food or animal feed. Several anti-nutritional factors limit the use of specific plant material in the preparation of animal feed and food for humans. Plant material containing lignocellulosic material such as cellulose greatly reduces the digestibility of the plant material by the animals. This effect is reduced through the use of cellulosic degrading enzymes, namely mutant thermostable enzymes, which permit a higher proportion of plant material to be converted to feed, resulting in a reduction of feed costs. Additionally, through the activity of the thermostable enzymes, cellulosic material is broken down to simpler sugars, which can be more readily assimilated to provide additional energy. Accordingly, compositions comprising the enzymes of the present disclosure are preferably used for processing and/or manufacturing of food or animal feed.

The provided enzymes of the present disclosure are useful as additives to feed for mono-gastric animals such as poultry and swine, as well as for human food. In some embodiments, the enzymes are used to pre-treat the feed instead of as a feed additive. In some preferred embodiments, the enzymes are added to or used to pre-treat feed for weanling pigs, nursery pigs, piglets, fattening pigs, growing pigs, finishing pigs, laying hens, broiler chicks, and/or turkeys. In some embodiments, the enzymes are added to or used to pre-treat feed from plant material such as palm kernel, coconut, konjac, locust bean gum, gum guar, soy beans, barley, oats, flax, wheat, corn, linseed, citrus pulp, cottonseed, groundnut, rapeseed, sunflower, peas, and lupines.

Because of their thermostability, the enzymes find use in processes of producing pelleted feed in which heat is applied to the feed mixture before the pelleting step, as it is the case in most commercial pellet mills. In one example, the enzymes are added to the other feed ingredients in advance of the pelleting step or after the pelleting step to the already formed feed pellets.

In compositions comprising the enzymes intended for food processing or as a feed supplement, the compositions optionally contain other substituents such as coloring agents, aroma compounds, stabilizers, vitamins, minerals, other feed or food enhancing enzymes and the like. This applies in particular to the so-called pre-mixes. Food additives according to this present disclosure may be combined with other food components to produce processed food products. The resulting, combined food additive is mixed in an appropriate amount with other food components such as cereal or plant proteins to form a processed food product.

Textile Cleaning and Detergents

The provided enzymes, methods, and compositions also find use in textile methods, including cleaning, cotton softening, and denim finishing, the polishing of cotton fabrics under high temperature treatments, and in production and uses of detergents, for example, for color care, cleaning, and anti-deposition. For example, the enzymes find use in detergent compositions to facilitate the removal of cellulose-containing stains and soils. In one embodiment, the enzymes are used in detergent compositions; provided are such detergent compositions and methods for their use. In one embodiment, the detergent compositions contain the enzymes in combination with other enzymes from the group of amylases, mannases, cellulases, lipases, pectinases, proteases, endoglucanases, and exoglucanases.

Detergent compositions of the present disclosure comprising the enzymes are in any convenient form (e.g., a bar, a tablet, a powder, a granule, a paste or a liquid). A liquid detergent is generally aqueous, typically containing up to 70% water and 0-30% organic solvent(s), or non-aqueous component(s).

The detergent composition comprises one or more surfactants (e.g., non-ionic including semi-polar, anionic, cationic and/or zwitterionic). The surfactants are typically present at a level of from 0.1% to 60% by weight. When included, detergents typically contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid, or soap. When included, detergents typically contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine (glucamides).

Detergent compositions optionally comprise 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic add, soluble silicates, or layered silicates. Detergent compositions optionally comprise one or more polymers such as carboxymethylcellulose (CMC), poly(vinylpyrrolidone), poly(ethylene glycol), poly(vinyl alcohol), poly(vinylpyridine-N-oxide), poly (vinylimidazole), polycarboxylates such as polyacrylates, maleic/acrylic acid copolymers, and lauryl methacrylate/acrylic acid copolymers. The detergent optionally comprises a bleaching system (e.g., hydrogen peroxide source) such as perborate or percarbonate, which may be combined with a peracid-forming bleach activator such as tetraacetylethylenediamine or nonanoyloxybenzenesulfonate. Alternatively, the bleaching system comprises peroxyacids of the amide, imide, or sulfone type.

In one embodiment, the enzymes are added in an amount corresponding to 0.01-100 mg of enzyme protein per liter of wash liquor, preferably 0.05-5 mg of enzyme protein per liter of wash liquor, in particular 0.1-1 mg of enzyme protein per liter of wash liquor.

Paper Pulp Processing

In another embodiment, the provided compositions and enzymes find use in pulp and paper methods, such as in paper pulp bleaching, deinking, drainage improvement, and fiber modification, for example, in high temperature applications for the pulping of cellulolytic materials. Provided are methods and compositions for use of the provided enzymes for such purposes. For example, in some embodiments, the enzymes find use in the enzyme-aided bleaching of paper pulps such as chemical pulps, semi-chemical pulps, kraft pulps, mechanical pulps or pulps prepared by the sulfite method. In some embodiments, the pulps are chlorine free pulps bleached with oxygen, ozone, peroxide or peroxyacids. In some embodiments, the enzymes are used in enzyme-aided bleaching of pulps produced by modified or continuous pulping methods that exhibit low lignin contents. In some embodiments, the enzymes are applied alone; in other embodiments, they are provided in combination with other enzymes, such as xylanase and/or endoglucanase and/or alpha-galactosidase and/or cellobiohydrolase enzymes.

The following examples are offered to illustrate provided embodiments and are not intended to limit the scope of the invention.

EXAMPLES

Example 1

Mutagenesis of Trichoderma reesei Endoglucanase I

Figure 1B:
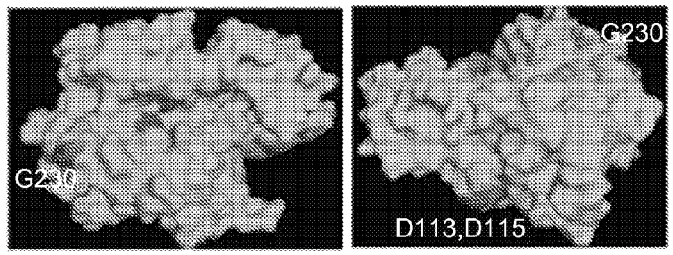

*Trichoderma reesei* endoglucanase I (TrEGI) was initially selected for engineering enhanced thermostability because the crystal structure of this enzyme is available and it is the most abundant endoglucanase produced by *T. reesei*. The initial approach for improving the thermostability of TrEGI relied on using a B-factor guided approach (B-FIT method) (Reetz, M T et al., *Angew Chem Int Ed Engl* 45(46):7745-51, 2006). The B-factors, obtained from crystal structure, are a measure of residue mobility in a polypeptide. In this approach, residues that had the highest average B-factors corresponding to the most flexible sites were selected for mutagenesis to obtain improved thermostability. This approach was based on the assumption that the thermostability of a mesophilic enzyme can be enhanced by increasing rigidity at the most flexible sites in its structure. Using the crystal structure of the TrEGI enzyme, 20 residues with the highest B-factor values were identified (Table 1). Seven sites, which were comprised of one or more amino acids, were selected {Site A (aa 284-287), Site B (aa 301-302), Site C (aa 113, 115), Site D (aa 238), Site E (aa 230), Site F (aa 323), Site G (aa 291)} for mutagenesis (FIG. 1; Table 1).

Table 1 shows residues in *T. reesei* EGI with the highest B-factor values.

| Residue | Number | Mutation Site | B-factor | B-factor Rank |
|---------|--------|---------------|----------|---------------|
| GLY | 287 | A | 99.6 | 1 |
| GLY | 286 | A | 98.8 | 2 |
| ASN | 265 | — | 95.3 | 3 |
| THR | 371 | — | 84.2 | 4 |
| GLY | 238 | D | 83.8 | 5 |
| GLY | 230 | E | 77.1 | 6 |
| ASN | 276 | — | 77 | 7 |
| GLN | 284 | A | 76.9 | 8 |
| THR | 217 | — | 75.5 | 9 |
| GLN | 28 | — | 74.4 | 10 |
| GLY | 277 | — | 74.2 | 11 |
| ASN | 323 | F | 73.7 | 12 |
| SER | 291 | G | 72.8 | 13 |
| ASP | 113 | C | 72 | 14 |
| ASP | 115 | C | 71.8 | 15 |
| PRO | 285 | A | 70.9 | 16 |
| LEU | 302 | B | 70.7 | 17 |
| ASP | 366 | — | 70.5 | 18 |
| LYS | 18 | — | 69.7 | 19 |
| GLY | 301 | B | 69.2 | 20 |

Cloning of *T. reesei* Endoglucanase I

The gene for TrEGI (cel7b, UniProt No. P07981) synthesized with *Escherichia coli* codon bias was purchased from GenScript (GenScript Corporation, Piscataway, N.J., USA). The gene was PCR-amplified from plasmid pUC57-P07981 by using the forward primer (5'-AAAAAACATATGCAA-CAACCGGGCACCTCC-3') (SEQ ID NO: 2) and reverse primer (5'-AAAAAAGTCGACTTACAGACATTGCGAG-TAGTA-3') (SEQ ID NO: 3). The PCR product was then cloned into pIVEX2.4d vector (Roche Applied Science, Indianapolis, Ind., USA) after a double digestion with NdeI and SalI to generate the plasmid, pIVEX2.4d-TrEG1. The sequencing of the cloned gene was performed at Elim Biopharmaceuticals (Hayward, Calif., USA).

Site-Directed Mutagenesis of *T. reesei* EGI

Site directed mutagenesis at amino acids 238, 291, and 323 of *T. reesei* EGI (pIVEX2.4d-TrEG1 as template plasmid) was performed using a site-directed mutagenesis kit (Stratagene, La Jolla, Calif., USA) by following the manufacturers' protocol with primers shown in Table 2.

Table 2 shows the listing of primers using for mutagenesis of *T. reesei* EGI

| Primer Name | Mutation Site* | Sequence |
|-------------|----------------|----------|
| A-FWD | A | GGC GTC GAT ATT CCG TCC GCA NDT NDT NDT NDT GAC ACC ATC TCT AGT TGC CCG TCA GC (SEQ ID NO: 4) |
| A-REV | A | GCT GAC GGG CAA CTA GAG ATG GTG TCA HMA HMA HMA HMT GCG GAC GGA ATA TCG ACG CC (SEQ ID NO: 5) |
| B-FWD | B | TCA GCA TCG GCC TAC GGC NNK NNK GCA ACC ATG GGC AAA GCT C (SEQ ID NO: 6) |

-continued

| Primer Name | Mutation Site* | Sequence |
|---|---|---|
| B-REV | B | GAG CTT TGC CCA TGG TTG CMN NMN NGC CGT AGG CCG ATG CTG A (SEQ ID NO: 7) |
| C-FWD | C | CGC GTC TGT ATC TGC TGN NKT CTN NKG GCG AAT ACG TGA TGC TG (SEQ ID NO: 8) |
| C-REV | C | CAG CAT CAC GTA TTC GCC MNN AGA MNN CAG CAG ATA CAG ACG CG (SEQ ID NO: 9) |
| D-FWD | D | CAA ATC CTA TTA CNN KCC GGG TGA TAC C (SEQ ID NO: 10) |
| D-REV | D | GGT ATC ACC CGG MNN GTA ATA GGA TTT G (SEQ ID NO: 11) |
| E-FWD | E | GTT TCA ACC CGT ATN NKA GTG GTT ACA AAT C (SEQ ID NO: 12) |
| E-REV | E | GAT TTG TAA CCA CTM NNA TAC GGG TTG AAA C (SEQ ID NO: 13) |
| F-FWD | F | CAA TTT GGA ACG ATN NKT CGC AGT ATA TG (SEQ ID NO: 14) |
| F-REV | F | CAT ATA CTG CGA MNN ATC GTT CCA AAT TG (SEQ ID NO: 15) |
| G-FWD | G | GAC ACC ATC TCT NNK TGC CCG TCA G (SEQ ID NO: 16) |
| G-REV | G | CTG ACG GGC AMN NAG AGA TGG TGT C (SEQ ID NO: 17) |
| T7-FWD | Universal FWD | TCG ATC CCG CGA AAT TAA TAC GAC TCA CTA TAG GG (SEQ ID NO: 18) |
| T7-REV | Universal REV | CAA AAA ACC CCT CAA GAC CCG TTT AG (SEQ ID NO: 19) |

*Site A: amino acids 284-287; Site B: amino acids 301-302; Site C: amino acids 113, 115; Site D: amino acid 238; Site E: amino acid 230; Site F: amino acid 323; Site G: amino acid 291

Mutagenesis at sites with amino acids 230, 113 & 115, 284-287 and 301-302 of *T. reesei* EGI (pIVEX2.4d-TrEG1 as template plasmid) was performed using OE-PCR. The products of the first PCR were generated using the plasmid template pIVEX2.4d-TrEG1 and primers (Table 1) that differed from the target sequence of EGI only at the places where mutagenesis was intended. Following gel purification, the PCR fragments were used as primers as well as template for the OE-PCR to construct the mutagenized *T. reesei* EGI genes. All PCR reactions were carried out using Pfu DNA polymerase (Stratagene). The optimum conditions for OE-PCR were as follows: one cycle of denaturation at 98° C. for 30 seconds, 30 cycles of denaturation at 98° C. for 10 seconds, annealing at 60° C. for 30 seconds, extension at 72° C. for 40 seconds, and the final extension at 72° C. for 5 minutes. This OE-PCR product was gel-purified and then used as the megaprimer with pIVEX2.4d-TrEG1 as the template plasmid for constructing the mutant EGI genes bearing pIVEX2.4d plasmid. All primers were kindly supplied by IDT (Integrated DNA Technologies Inc., Coralville, Iowa, USA; Table 2). The amount and purity of the PCR products were analyzed on 1.2% agarose gels. The sequencing of all chimeric genes was performed at Elim Biopharmaceuticals (Hayward, Calif., USA).

PCR of Mutant *T. reesei* EGI Genes

One μL of overnight cultures of cells containing mutant *T. reesei* EGI genes was used in the PCR reaction to generate template for cell-free EGI expression. Each reaction mixture consisted of 100 μM of T7 fwd and T7 rev primers, lx PCR buffer, 2.5 mM dNTP and 0.2 units of LA Taq polymerase, with a final total volume of 20 μL. The following protocol was used: one cycle of denaturation at 95° C. for 5 minutes, 30 cycles of denaturation at 95° C. for 20 seconds, annealing at 55° C. for 20 seconds, extension at 72° C. for 1 minute, and the final extension at 72° C. for 5 minutes.

Example 2

Cell-Free Synthesis of *T. reesei* EGI

A cell-free synthesis platform (Kim, T et al., *Biotechnol Bioeng* DOI: 10.1002/bit.22856, 2010) was used for protein expression of the *T. reesei* EGI mutants generated as described above.

Preparation of S30 Cell-Extract

The cell-extracts were prepared from *E. coli* strain BL21 Star™ (DE3) (Invitrogen, Carlsbad, Calif., USA) and its derivative strain [BL21 Star™ (DE3)-pGro7], according to the procedure of Pratt (Pratt, J M, *Transcription and translation: A practical approach,* 179, 1984) with some modifications. The chaperone plasmid pGro7 encoding GroEL/ES was purchased from Takara Bio (TAKARA BIO, Shiga, Japan). The cells were grown at 37° C. in 3 L of 2×YTPG medium (2×YT supplemented with 22 mM $NaH_2PO_4$, 40 mM $Na_2HPO_4$, and 100 mM glucose) with vigorous agitation and aeration. For cells harboring pGro7, 0.05% L-arabinose was added to the medium, and when the cell density ($OD_{600}$) reached 0.6, isopropyl-thiogalactopyranoside (IPTG, 1 mM) was added to induce expression of T7 RNA polymerase. The cells were harvested in mid-log phase ($OD_{600}$≈4.5) and were washed three times by suspending them in buffer A (20 mL per g of wet cells) and then centrifuged. Buffer A contained 10 mM Tris-acetate buffer (pH 8.2), 14 mM magnesium acetate, 60 mM potassium glutamate, and 1 mM dithiothreitol (DTT) containing 0.05% (v/v) 2-mercaptoethanol (2-ME). Before storing the pellets at −80° C., the wet cell pellets were weighed.

The thawed cells (10 g) were suspended in 12.7 mL of buffer B (buffer A without 2-ME) and disrupted in a French cell-press (Thermo Scientific, Waltham, Mass., USA) at a constant pressure of 20,000 psi. The lysate was then centrifuged at 30,000 g for 30 minutes at 4° C., and the supernatant was separated from the pellet fraction and then centrifuged again. The final supernatant was shaken at 100 rpm, and 3 mL of the pre-incubation solution (293.3 mM Tris-acetate pH 8.2, 2 mM magnesium acetate, 10.4 mM ATP, 200 mM creatine phosphate, 4.4 mM DTT, 0.04 mM amino acids, 26.7 µg/mL creatine kinase) was then added gradually to 10 mL of the supernatant, which was then incubated with gentle shaking at 37° C. for 80 minutes. The pre-incubated sample was dialyzed for 4×45 minutes each at 4° C. against 50 volumes of buffer B using a Pierce membrane (SnakeSkin™ Pleated Dialysis Tubing, Rockford, Ill., USA) with a molecular weight cut off (MWCO) of 10,000. The retained extract was centrifuged at 4,000 g for 10 minutes at 4° C. to obtain the supernatant. To exhaust the reducing activity of cell-extract, the S30 extract was incubated with 10 mM oxidized glutathione for 2 hours at 30° C. The residual glutathione molecules were removed by dialyzing the treated extract against 200 volumes of buffer C (buffer A without DTT and 2-ME) for 3 hours at 4° C. The resulting extract was divided into small aliquots and stored at −80° C. before using it for cell-free protein synthesis.

Protein Synthesis

The standard reaction mixture for cell-free protein synthesis consisted of the following components in a total volume of 15 µL: 57 mM of Hepes-KOH (pH 7.5); 1.2 mM of ATP; 0.85 mM each of CTP, GTP, and UTP; 0.17 mg/mL of *E. coli* total tRNA mixture (from strain MRE600); 90 mM of potassium glutamate; 80 mM of ammonium acetate; 12 mM of magnesium acetate; 34 µg/mL of L-5-formyl-5,6,7,8-tetrahydrofolic acid (folinic acid); 2.0 mM each of all 20 amino acids; 2% PEG (8000); 67 mM of creatine phosphate (CP); 3.2 µg/mL of creatine kinase (CK); 2.5 mM oxidized glutathione; 2.5 mM reduced glutathione; 150 µg/mL of DsbC; 16.7 µg/mL of PCR product; 27% (v/v) of S30-GroEL/ES cell-extract. The cell-free reaction was conducted at 30° C. for 2 hours. For determining the amount of protein synthesized using the cell-free synthesis, 10 µM of L[U-$^{14}$C] Leucine (11.3 GBq/mmol, Amersham Biosciences/GE Healthcare, Piscataway, N.J., USA); was also added to the cell-free reaction. To analyze the solubility of cell-free expressed protein, the cell-free mixture was centrifuged at 15,000 rpm for 10 minutes at 4° C. The soluble amount of synthesized protein was determined by analyzing the supernatant of the centrifugation. The amount of each cell-free synthesized cellulase was estimated from the TCA-insoluble radioactivity using a liquid scintillation counter (Tri-Carb 2810TR Liquid Scintillation Analyzer, Perkin-Elmer Inc., Waltham, Mass., USA), as described elsewhere (Kim, D M and Choi, C Y, *Biotechnol Prog* 12(5):645-649, 1996).

Redox Potential Optimization for the Cell-Free Expression of *T. reesei* EGI

TrEGI has 7 disulphide bonds. Expressing this enzyme under various redox potentials, obtained by varying the amount of reduced and oxidized glutathione while carrying out the cell-free synthesis, explored the redox space required to correctly form these disulphide bonds. The amount of oxidized glutathione and reduced glutathione in cell-free synthesis was varied as follows: oxidized glutathione:reduced glutathione—0:5, 1:4, 2:3, 3:2, 4:1 and 5:0 mM. The total concentration of glutathione was always kept at 5 mM in the cell-free synthesis reaction. The TrEGI enzymes synthesized under various redox conditions were spotted on CMC-plate. The plate was incubated overnight at 50° C. prior to staining with congo red.

Figure 2:
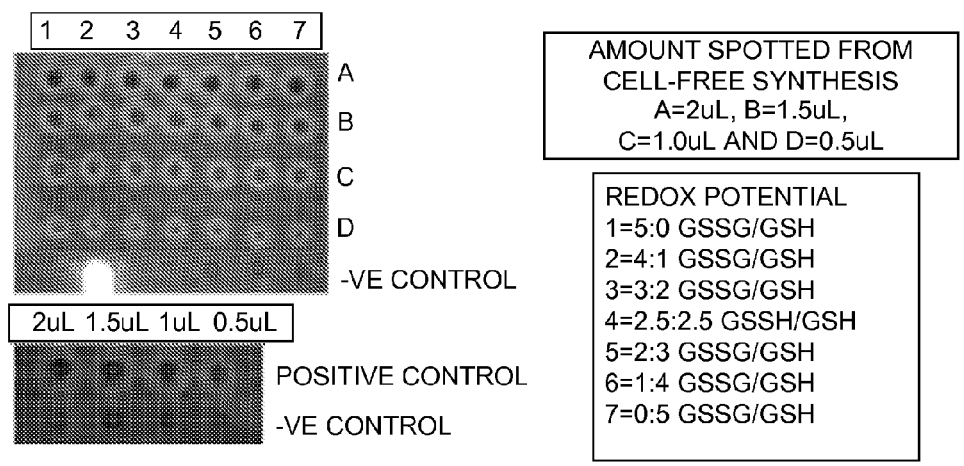
FIG. 2 shows redox potential optimization for cell-free expression of wild-type *T. reesei* EGI.

The results indicate that an active enzyme, consisting of correct disulphide formation, is obtained regardless of the redox potential of the cell-free expression reaction (FIG. 2).

Example 3

Screening of TrEGI Mutants with Improved Thermostability/Activity

The first step in the screening process was to identify conditions under which wild-type TrEGI loses all or most of its activity. These conditions were then used as the screening conditions to identify mutants with increased thermostability.

Selecting Screening Conditions for TrEGI Mutants

To measure the thermostability of wild-type TrEGI, 10 µL of the cell-free synthesized TrEGI (20 pmol) was mixed with 100 mM of sodium acetate buffer (pH 5.0). After incubating the enzyme mixture at various temperatures (45, 50, 55, 60, 65, 70° C.) for different lengths of time (0, 10, 20, 30, 40, 50, 60 minutes), 1.5% (w/v) CMC was added into the heat-pretreated enzyme mixture to start hydrolysis reaction for 1 hour at 50° C. The reducing sugar concentration was measured by the DNS method (Miller, G L, *Anal Chem* 31(3):426-428, 1959).

Thermostability of wild-type TrEGI was also tested by spotting on CMC-agar plates. Ten µL of the cell-free synthesized TrEGI (20 pmol) was mixed with 2 µL of 1 M of sodium acetate buffer (pH 4.85). After incubating the enzyme mixture at 53, 55, 57, 60, and 65° C. for different lengths of time (10, 30, 60 minutes), 2 µL of the enzyme mixture was spotted in the CMC-plate. The plate was incubated overnight at 50° C. prior to staining with congo red.

Figure 3A:
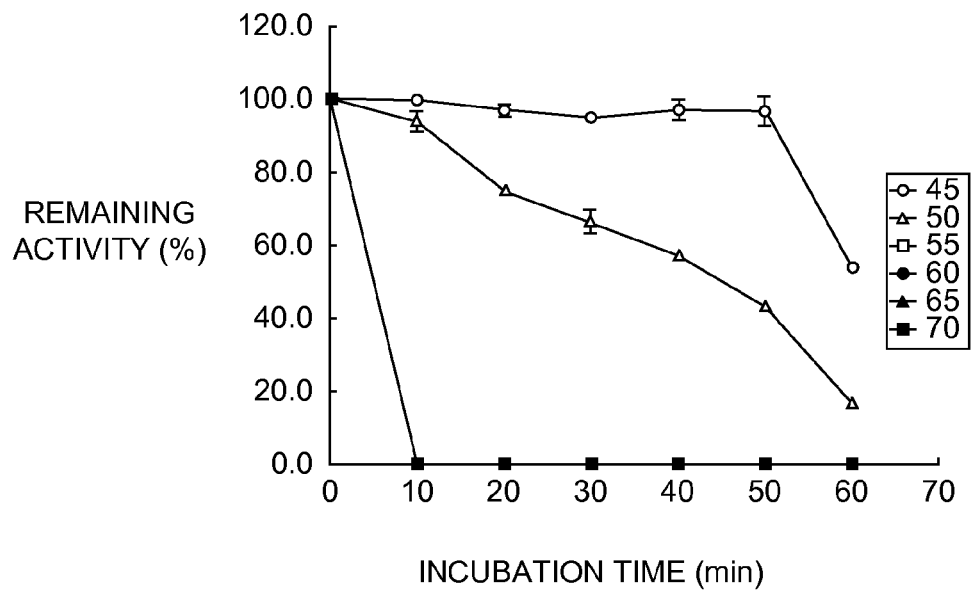
FIG. 3 shows activity of wild-type *T. reesei* EGI under various temperatures. (a) shows the activity of TrEGI after incubation at different temperatures for different lengths of time as measured by the DNS method. (b) shows the activity of TrEGI after incubation at different temperatures for different lengths of time as measured by spotting on CMC plate.
Figure 3B:
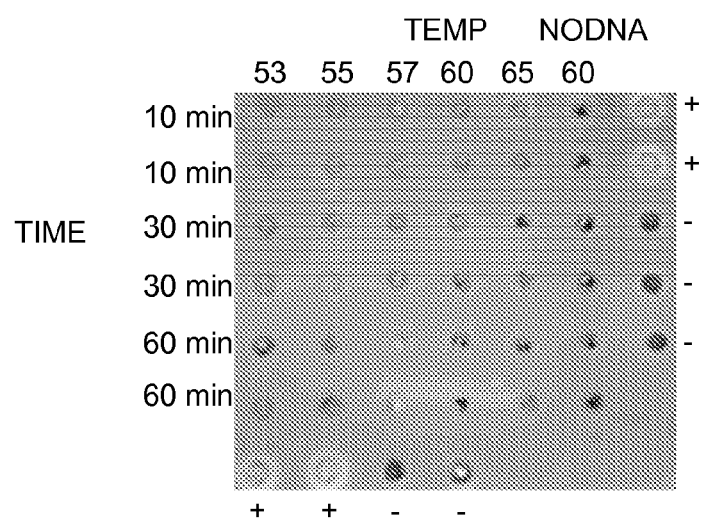

Based on the results as shown in FIG. 3, 50° C. pre-heating of the enzymes for 30 minutes was selected for the screening process for all the mutants since wild-type, parent TrEGI lost much of its activity under these conditions.

Figure 4:
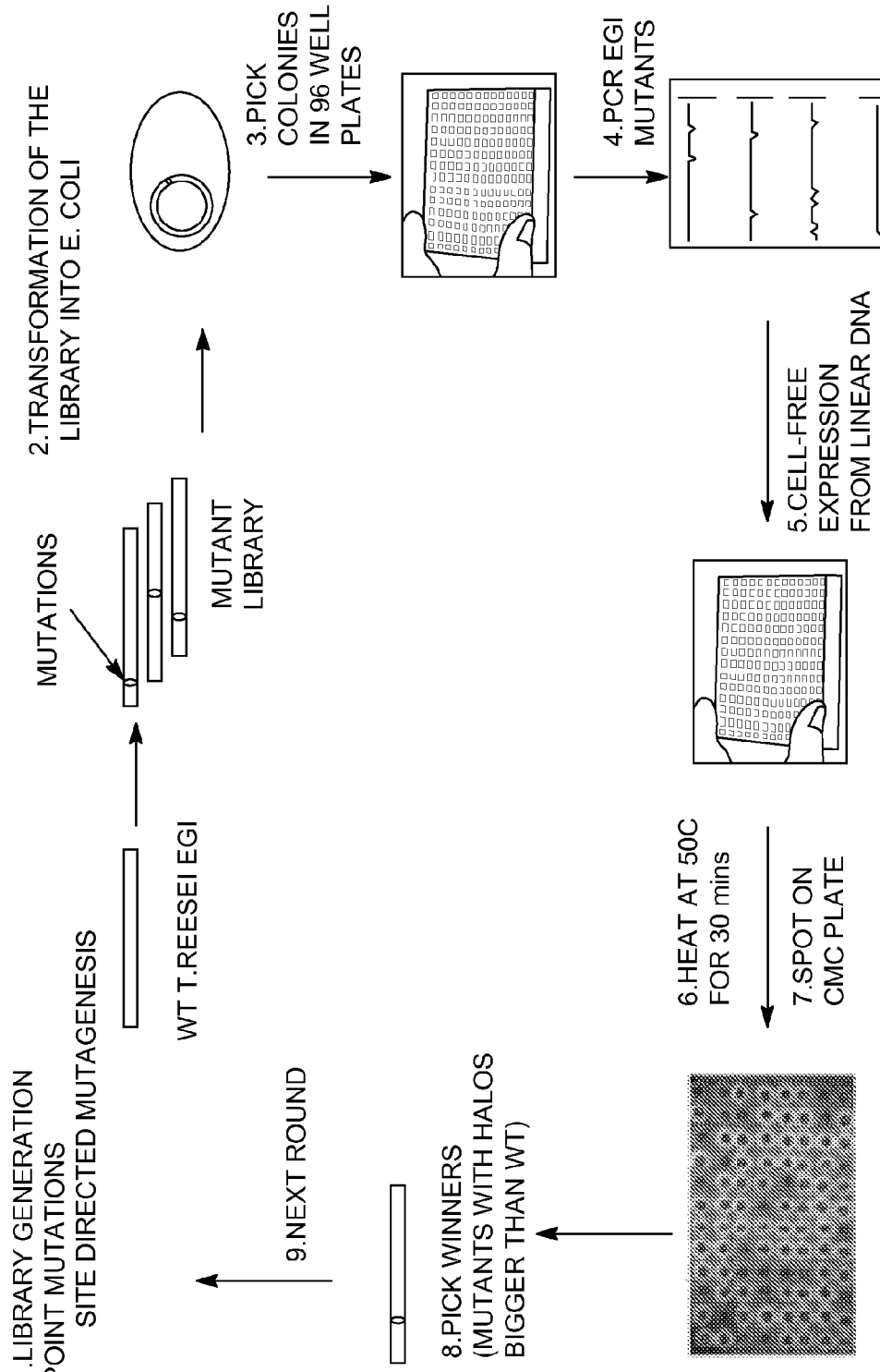
FIG. 4 shows the protocol for screening and selection of mutant *T. reesei* EGI for improved thermostability.

The protocol for screening and selection of mutant TrEGI enzymes is shown in FIG. 4 and described below.

Screening Process or Selectin TrEGI Mutants

Figure 5:
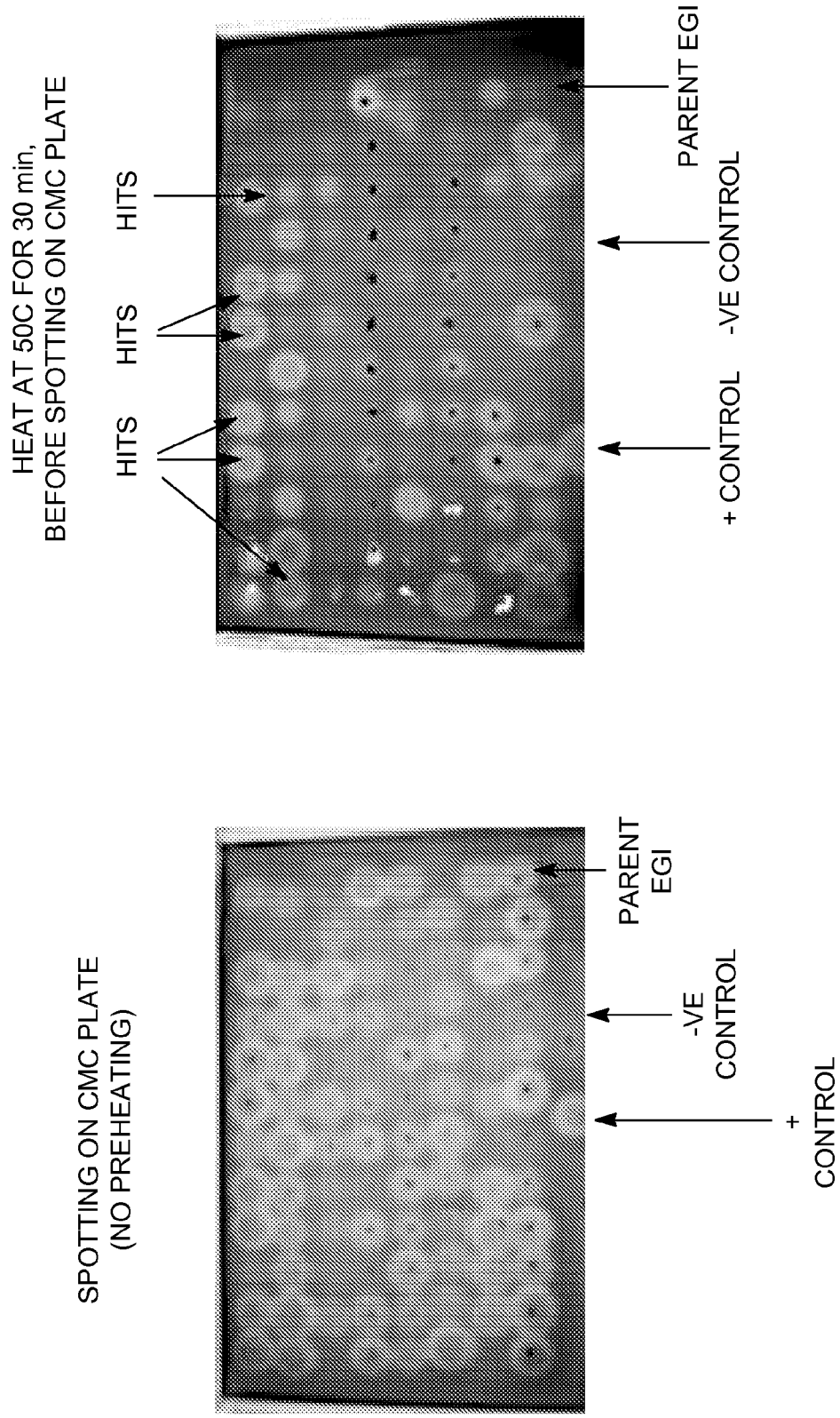
FIG. 5 shows the CMC plate assay of *T. reesei* EGI mutants before (left) and after (right) heat treatment.

The mutants were transformed in *E. coli* and plated. For each site (except site A), colonies corresponding to 95% coverage of sequence space were picked and grown overnight in deep-well 96-well plates. PCR of these clones was performed next in 96-well plates using the overnight culture as the template to afford ~300 ng/µL of linear TrEGI gene product, which was subsequently used for cell-free expression. To 15 µL of cell-free expressed TrEGI mutant, 2 µL of 1 M sodium acetate buffer pH 4.85 was added to lower the pH to around 5. TrEGI mutants were then heated to 50° C. for 30 minutes after which they were spotted on CMC-agar plate (1% CMC, 1.5% agar, 50 mM acetate buffer pH 4.85) and incubated overnight at 50° C. in an oven. Because the recombinant TrEGI expressed using cell-free synthesis lost all activity upon incubation at 50° C. for 30 minutes (FIG. 3), the cell-free expressed mutant TrEGI enzymes were incubated at 50° C. for 30 minutes prior to spotting on the CMC plate. The CMC-agar plates were stained the next day with 15 mL of 1% congo red for 5 minutes. Mutants having higher thermostability than the parent remained active after the heat treatment and hence produced a halo or clearing zone on the CMC plate stained with congo red. Thus, the plates were analyzed for active enzymes (hits), which can be used as parents for subsequent rounds of mutagenesis. Mutagenesis at sites A-G generated ~500 mutants with improved thermostability at 50° C. relative to the recombinant TrEGI (FIG. 5; Table 3)
Table 3 shows results of screening of *T. reesei* EGI mutants

| Mutation Site | Amino Acids | No. of mutants for 95% coverage | No. of mutants screened | PCR | No. of mutants with improved thermostability |
|---|---|---|---|---|---|
| A | 284-287 | 3.00E+07 | 3500 | Done | ~500 |
| B | 301-302 | 3000 | 3000 | Done | |
| C | 113, 115 | 3000 | 3000 | Done | |
| D | 238 | 300 | 400 | Done | 5 |
| E | 230 | 300 | 300 | Done | 7 |
| F | 323 | 300 | 300 | Done | 3 |
| G | 291 | 300 | 300 | Done | 2 |

Example 4

Characterizing *T. reesei* EGI Mutants with Improved Thermostability

Mutants identified by the screen were tested for increased thermostability by measuring CMC hydrolysis upon incubation with the TrEGI mutants.
Measuring Activity/Thermostability of *T. reesei* EGI Mutants To measure the activity/thermostability of TrEGI mutants, 10 µL of the cell-free synthesized enzyme (20 pmol) was mixed with 100 mM of sodium acetate buffer (pH 4.85). After incubating the enzyme mixture at 50° C. for different lengths of time (0, 15, 30, 45, 60 minutes), 1.1% (w/v) CMC was added into the heat-pre-treated enzyme mixture to start hydrolysis reaction for 1 hour at 50° C. The reducing sugar concentration was measured by the DNS method (Miller, G L, *Anal Chem* 31(3):426-428, 1959).

Figure 6:
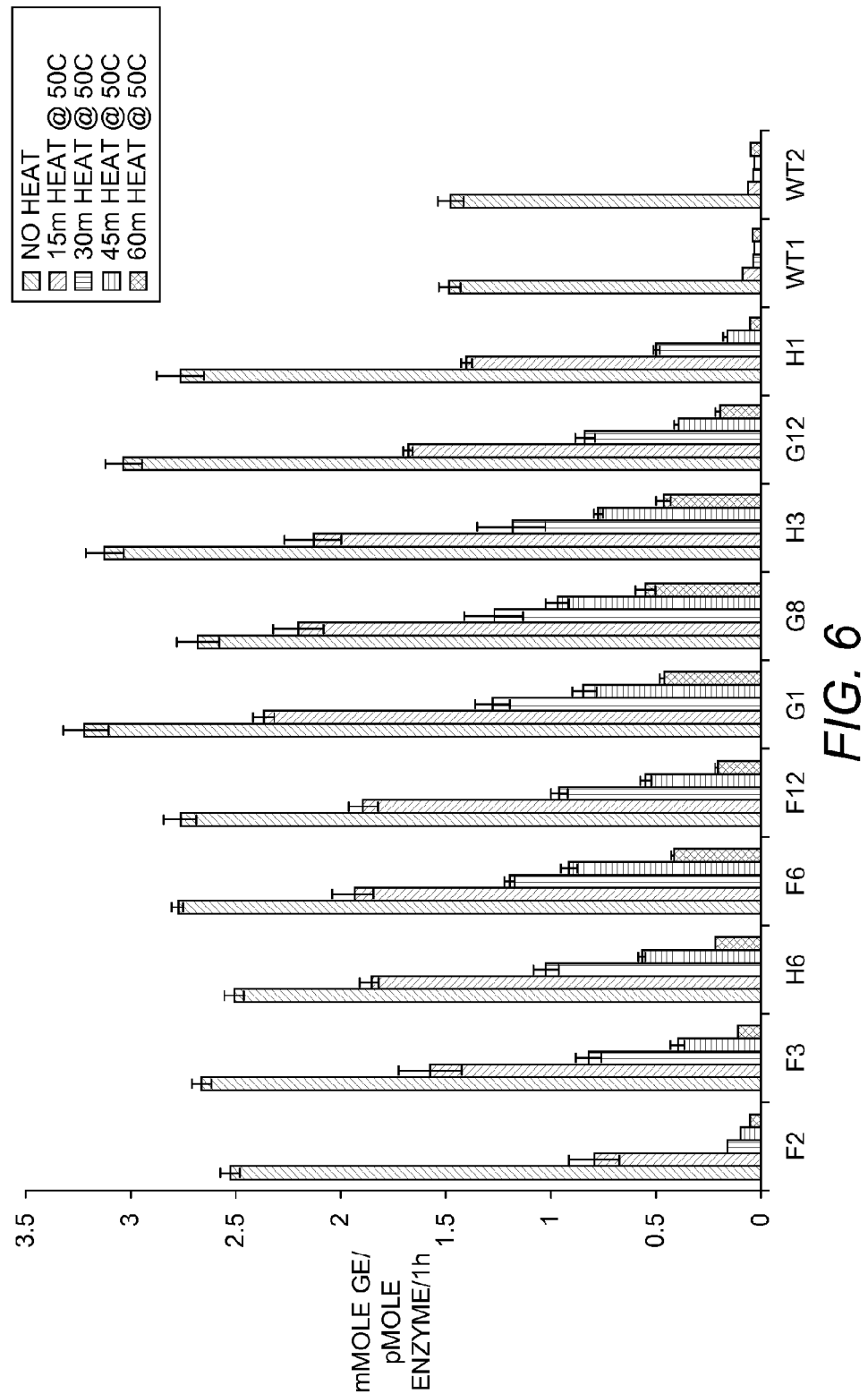
FIG. 6 shows the effect of heat treatment for different lengths of time on the activity of *T. reesei* EGI mutants identified by the screening process. The mutants are labeled in the y-axis according to their position in the 96-well plate.

As the results shown in FIG. 6 indicate, the tested mutants had increased activity compared to cell-free synthesized wild-type TrEGI. The effect of the mutations on TrEGI thermostability is particularly dramatic in samples that were heated for longer lengths of time prior to addition of CMC. The mutated residues in the TrEGI enzymes were identified by sequencing: the F2, F3, H6, and F6 mutants consist of a G230E/V119M/Q93H mutation, the F12 mutant consists of a G230Q mutation, the G1 mutant consists of a G230K mutation, the G8 and H3 mutants consist of a G230A mutation, the G12 mutant consists of a G230X mutation, and the H1 mutant consists of a G230S mutation.

Figure 7A:
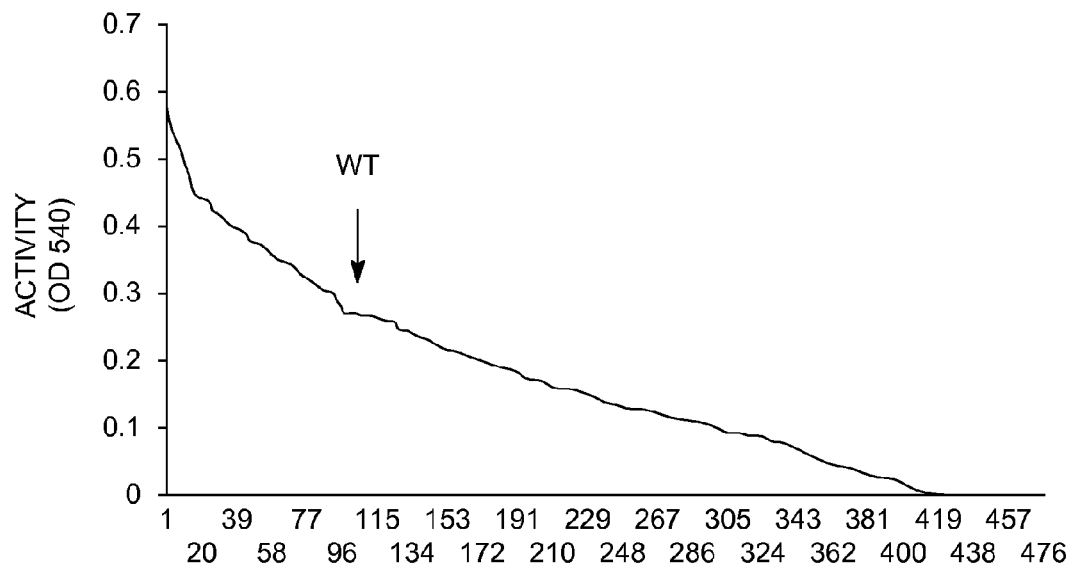
FIG. 7 shows activity of *T. reesei* EGI mutants, assayed before (a) and after (b) heat treatment at 50° C. for 45 minutes. The y-axis shows the number of mutants tested.
Figure 7B:
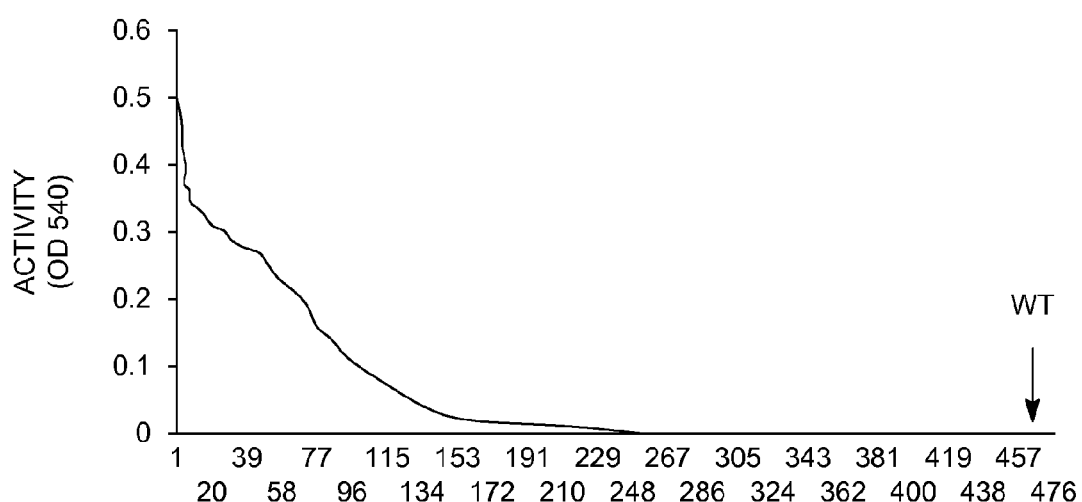
Figure 8:
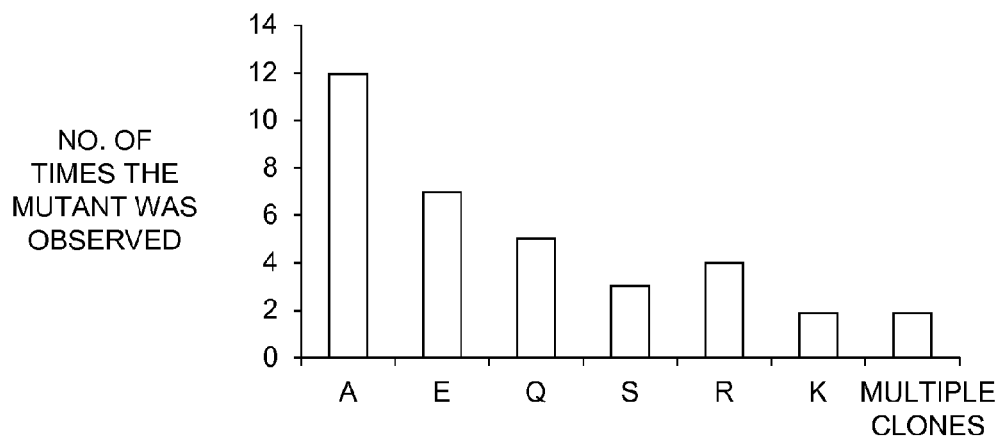
FIG. 8 shows the substitutions at G230 of *T. reesei* EGI resulting in increased thermostability.
Figure 9:
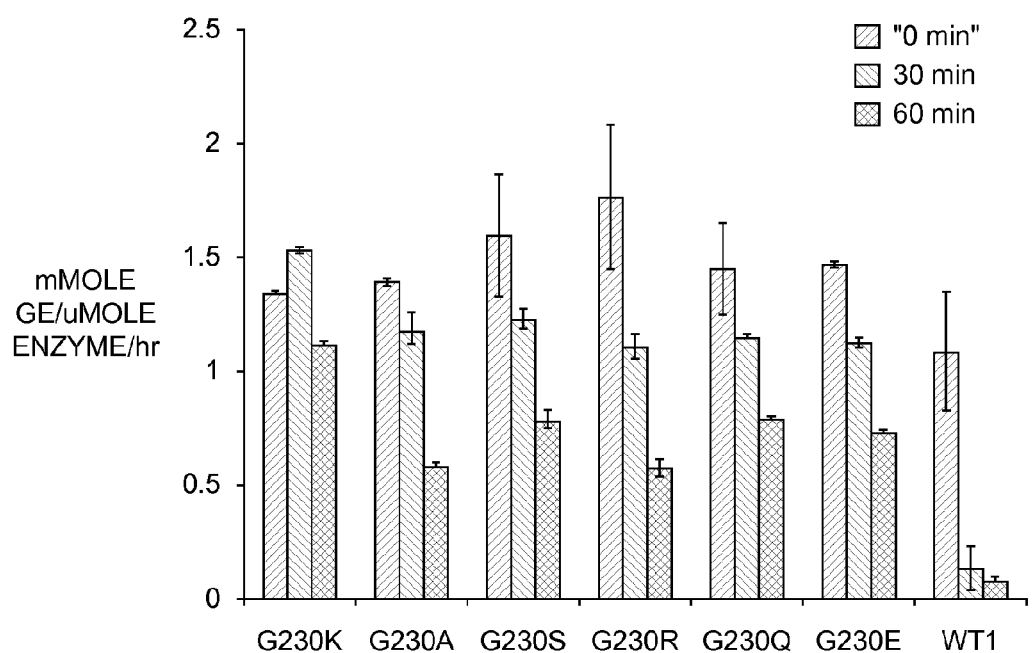
FIG. 9 shows the effect of different mutations at amino acid 230 on thermostability of *T. reesei* EGI at 50° C. Different series represent different incubation times at 50° C. prior to activity measurement. GE indicates "Glucose Equivalents".

FIG. 7 shows the results of all the mutants tested with (a) and without (b) heat treatment at 50° C. for 45 minutes at prior to assay. As indicated, a group of mutant enzymes had better thermostability than wild-type TrEGI.
Mutation at Site E (G230) of *T. reesei* EGI Sequencing of 70 mutants that showed high retained activity after incubation at 50° C. for 30 minutes revealed that all but six mutants had a mutation at site E (amino acid 230, glycine). Alanine, arginine, serine, threonine, leucine, lysine, glutamic acid, glutamine, and methionine substitutions at site E in place of the natural glycine residue led to improved thermostability, some of which are shown in FIG. 8. Specific activities of some of these mutants before and after heat treatment at 50° C. for various lengths of time are summarized in FIG. 9. The protocol described above was used to measure activity. The most stable mutant, G230K, retained about 80% activity after incubation at 50° C. for 1 hour, as compared to the parent TrEGI, which lost all of its activity under these conditions.

Mutation at Site C (D113, D115) of *T. reesei* EGI

Figure 10:
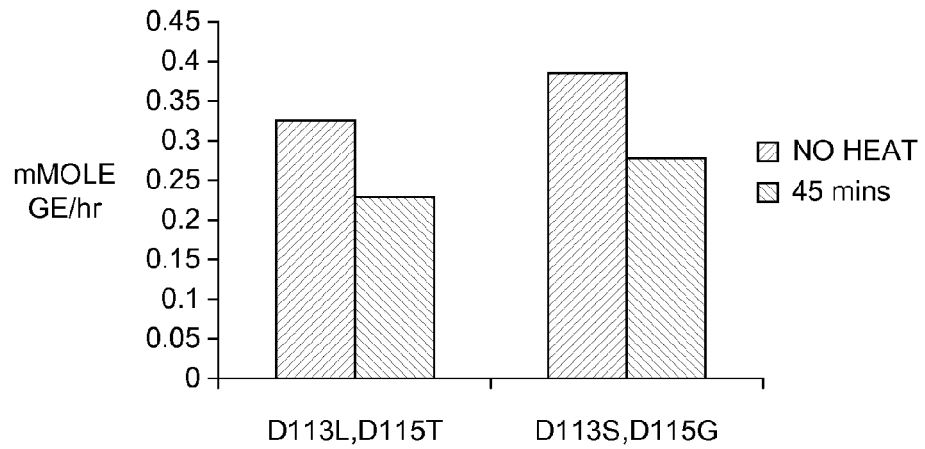
FIG. 10 shows the effect of heat treatment on the activity of *T. reesei* EGI with mutations at Site C (amino acids 113 and 115). GE indicates "Glucose Equivalents".

In addition, mutations at Site C (aa 113, 115) were shown to give rise to more thermostable variants of TrEGI (~80% activity retained upon heat treatment) Amino acid substitutions that gave rise to thermostable TrEGI mutants at this site were D113S, D113L, D115T, and D115G. The *T. reesei* EGI double mutants D113L/D115T and D113S/D115G are active with and without heat treatment at 50° C. as shown in FIG. 10.
Mutations at Sites E (G230) and C (D113, D115) of *T. reesei* EGI Thermostability of TrEGI variants with multiple mutations (Table 4) was tested as per the protocol described above. The enzyme concentration was 0.15-0.3 µM.

Table 4 shows 18 different triple mutants of *T. reesei* EGI obtained by combining 9 substitutions at G230 and 2 substitutions at D113/D115.

| Mutant No | AA @ 230 | AA @ 113,115 |
|---|---|---|
| 1 | G230K | D113SD115T |
| 2 | G230A | D113SD115T |
| 3 | G230S | D113SD115T |
| 4 | G230R | D113SD115T |
| 5 | G230Q | D113SD115T |
| 6 | G230E | D113SD115T |
| 7 | G230L | D113SD115T |
| 8 | G230M | D113SD115T |
| 9 | G230T | D113SD115T |
| 10 | G230K | D113LD115G |
| 11 | G230A | D113LD115G |
| 12 | G230S | D113LD115G |
| 13 | G230R | D113LD115G |
| 14 | G230Q | D113LD115G |
| 15 | G230E | D113LD115G |
| 16 | G230L | D113LD115G |
| 17 | G230M | D113LD115G |
| 18 | G230T | D113LD115G |

Figure 11:
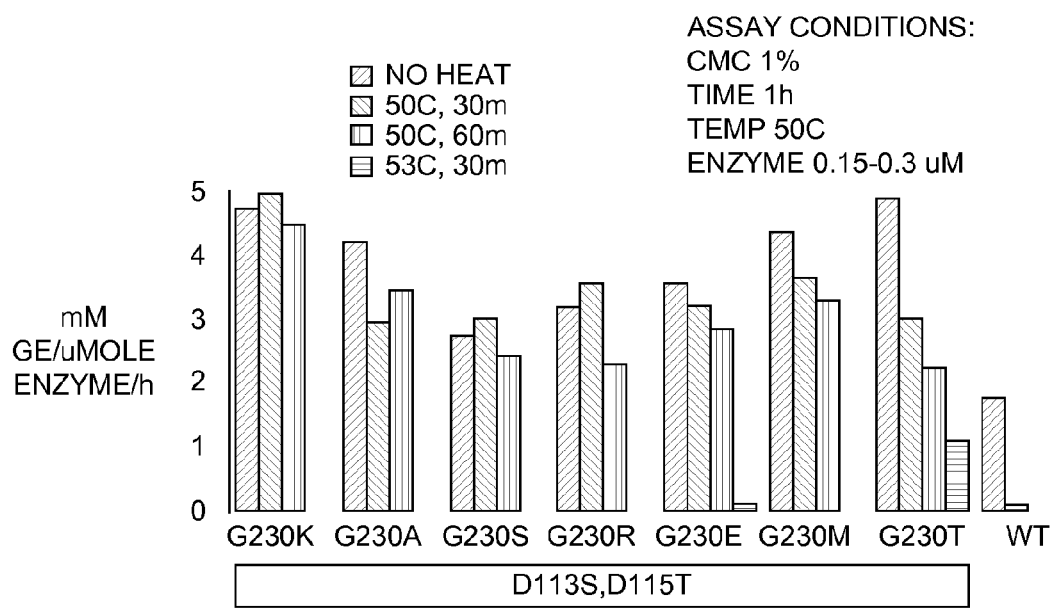
FIG. 11 shows the effect of mutations at amino acids 230, 113, and 115 on thermostability of *T. reesei* EGI at 50 and 53° C. The mutants were heat-treated for different lengths of time. GE indicates "Glucose Equivalents".

TrEGI variants with mutations at three amino acids D113S, D115T, and G230X (X=K, A, S, R, E, M, or T) (Table 4) demonstrated increased thermostability compared to wild-type TrEGI (FIG. 11). The triple mutants also had increased specific activity relative to single G230 mutants. Additionally, the TrEGI variant G230T/D113S/D115T showed activity after treatment at 53° C. for 30 minutes. The double TrEGI mutant with substitutions D113L/D115G and triple TrEGI mutants containing these substitutions (mutant numbers 10-18 in Table 4) did not show substantial activity at 50° C.

To summarize, experimental results indicate that substitutions at amino acid residue 230 and/or 113 and/or 115 in *Trichoderma reesei* Endoglucanase I improve the thermostability of the enzyme. Changes to different amino acids at this position resulted in mutant enzymes with much improved thermostability compared to the parent enzyme at temperatures of 50° C. or higher. This increase in thermostability allowed the mutant enzymes to remain active for longer periods of time at higher temperatures, thereby allowing higher overall conversions of substrate to product.

Example 5

*T. reesei* EGI Mutant Activity on Cellulosic Substrates

Figure 12:
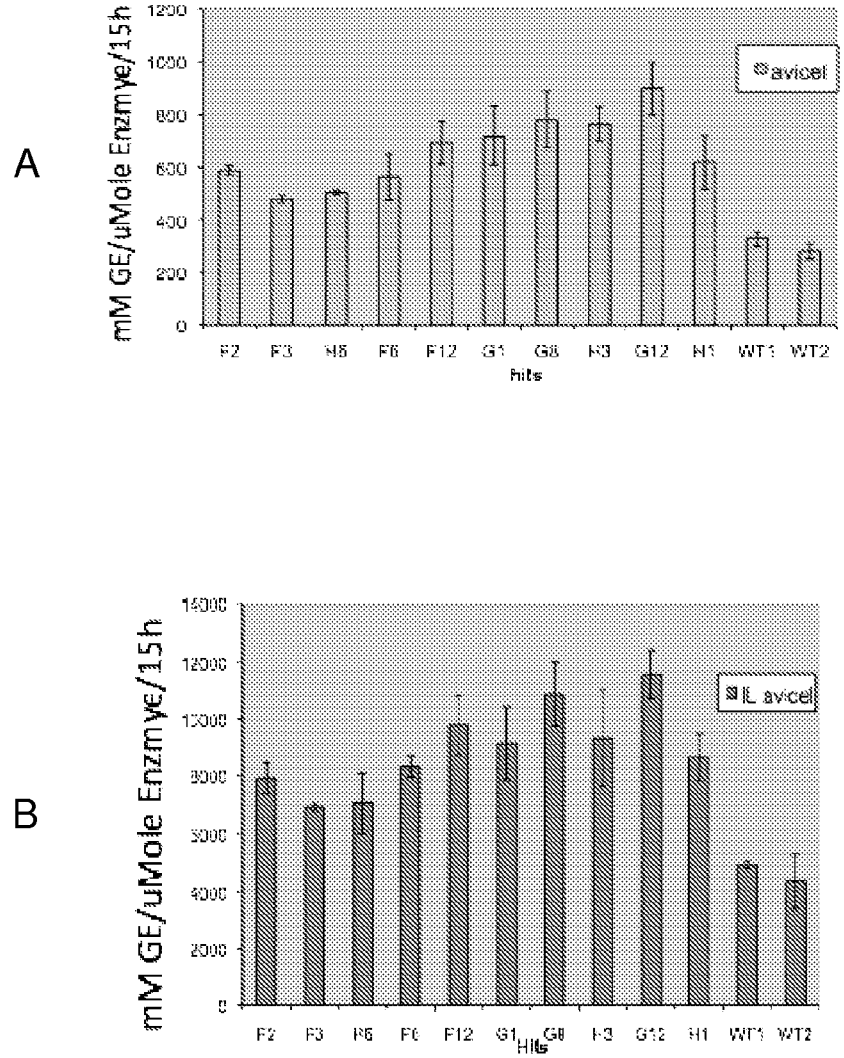
FIG. 12 shows the activity of *T. reesei* EGI mutants on different cellulosic substrates. (a) and (c) show activity on Avicel® and (b) and (d) show activity on IL-Avicel®. GE indicates "Glucose Equivalents".
Figure 12C:
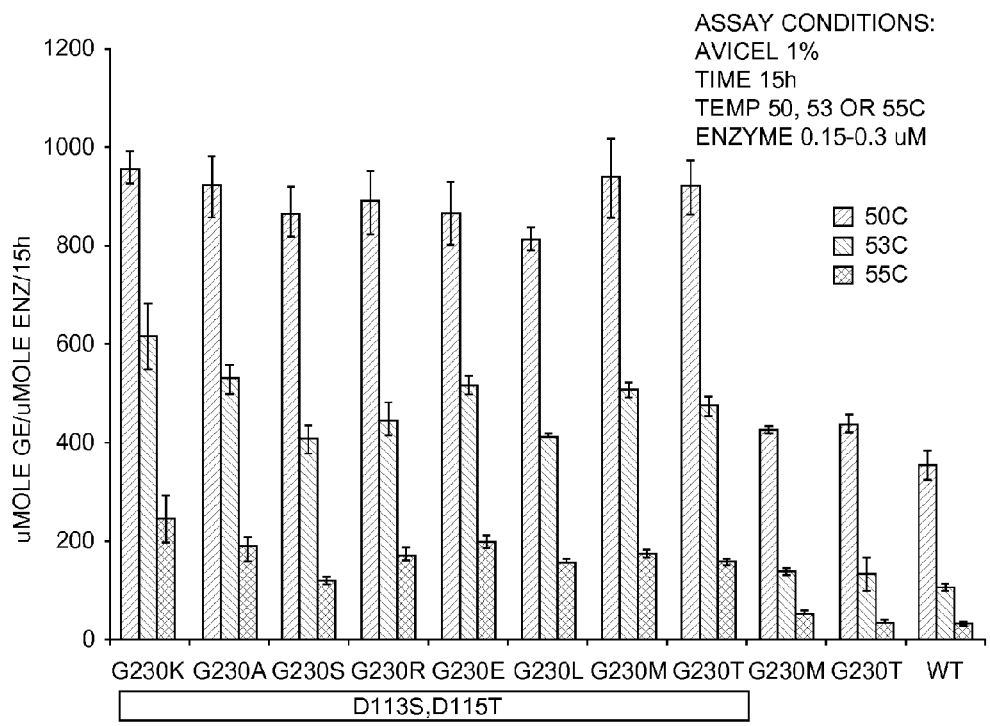
Figure 12D:
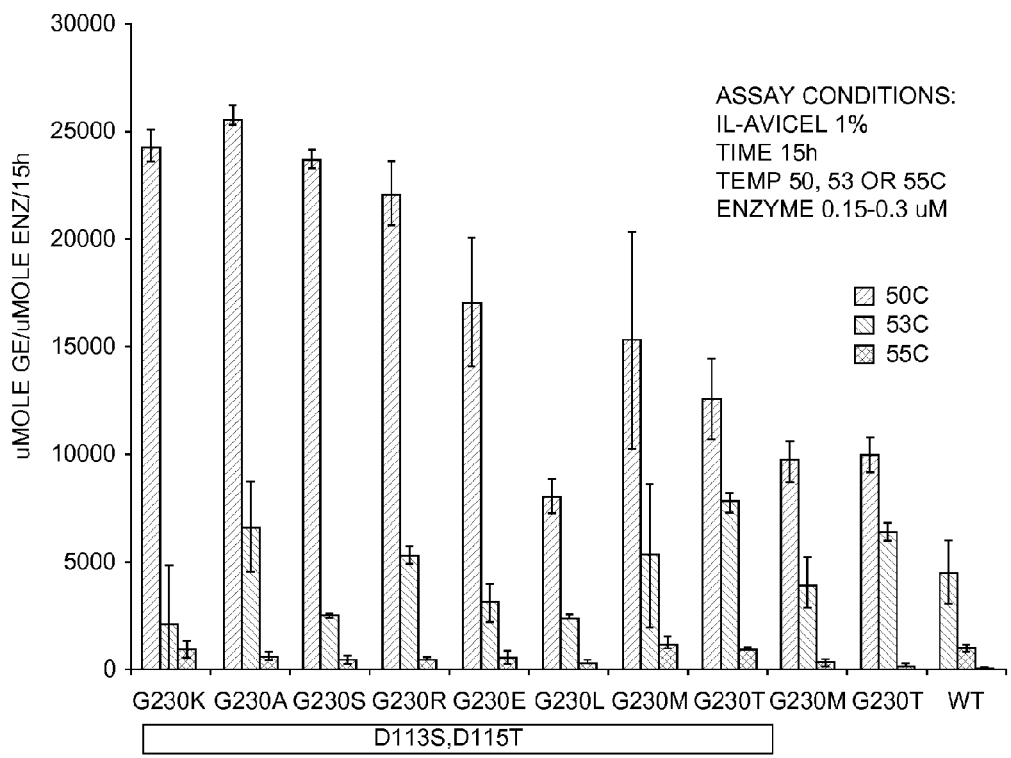
Figure 13A:
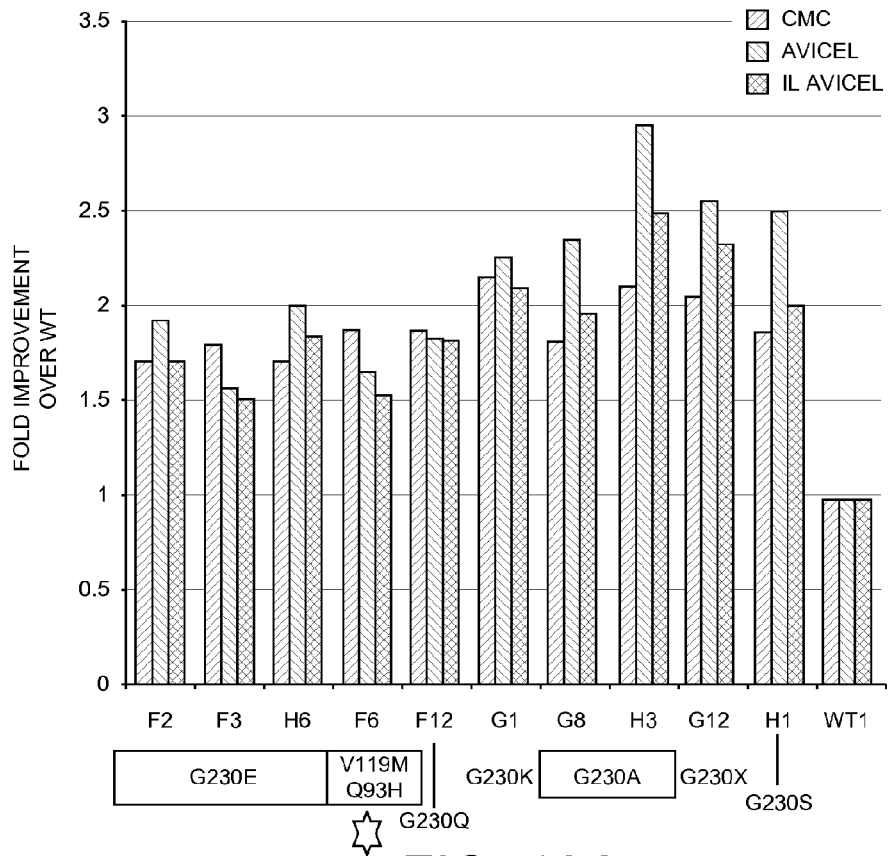
FIG. 13 shows a comparison of activity of *T. reesei* EGI mutants on substrates. (a) shows a comparison of activity on CMC, Avicel®, and IL-Avicel®. (b) shows a comparison of activity on Avicel®. (c) shows a comparison of activity on IL-Avicel®. GE indicates "Glucose Equivalents".
Figure 13B:
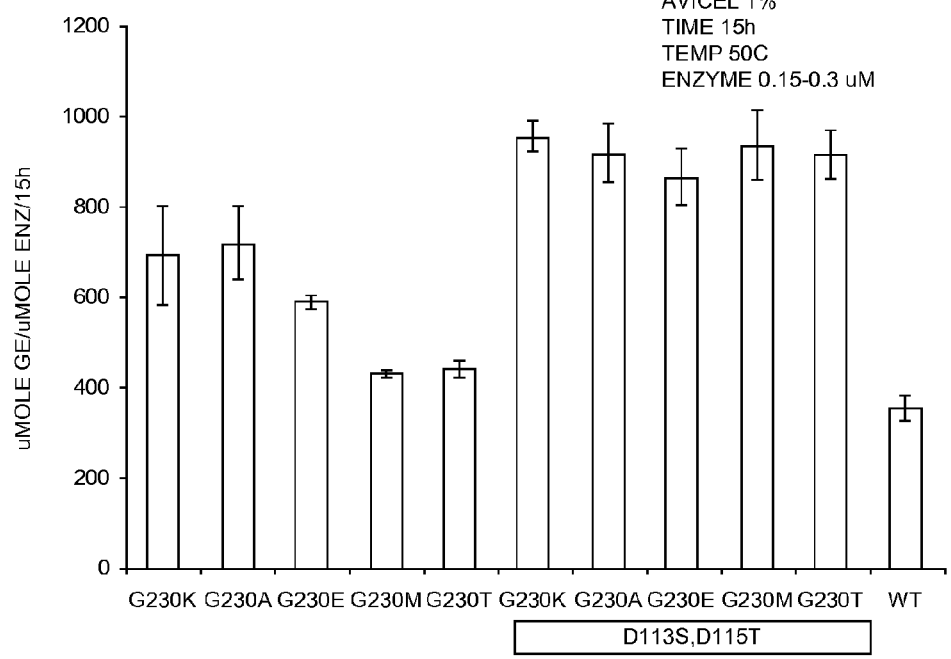
Figure 13C:
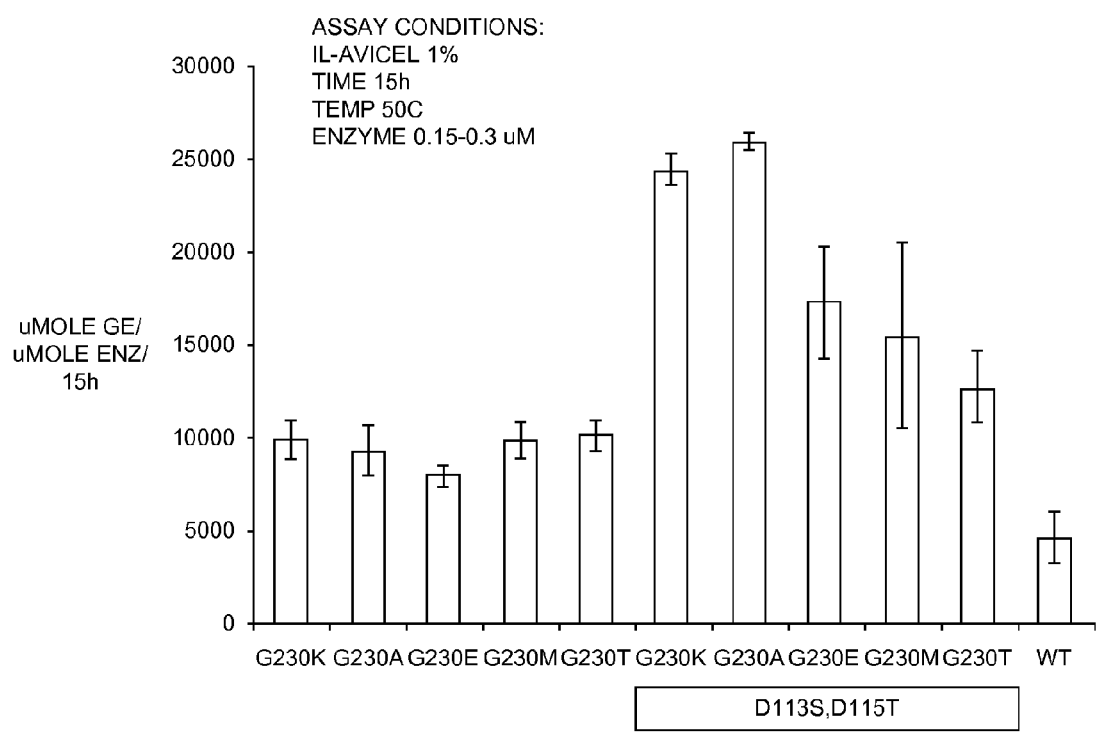

The effect of the TrEGI mutants on different cellulosic substrates was also tested (FIGS. 12 and 13).

Endoglucanase Activity Measurement on Insoluble Cellulosic Substrates

All cellulolytic assays for insoluble substrates were carried out in duplicate in 96-well plates in a final volume of 70 μL containing 1% (w/v) substrate, 100 mM sodium acetate buffer pH 4.85, 0.15-0.3 μM of the cellulase at 50, 53, or 55° C. The 96-well plates were sealed with aluminum foil and incubated in a thermocycler with heated top to minimize evaporation. Cellulase activities were measured for Avicel®, and ionic-liquid pre-treated Avicel® (IL-Avicel®). The mixtures were incubated at 50, 53, or 55° C. for 15 hours after which they were cooled to 4° C. prior to measuring the amount of soluble reducing sugar released using the glucose oxidase-peroxidase assay described below.

Glucose Oxidase Peroxidase Assay

The amount of soluble sugar released was measured using the glucose oxidase-peroxidase assay with Amplex Red as the substrate. Briefly, 8 μL of the supernatant from the hydrolysis reaction was incubated with 8 μL of β-glucosidase (5 mg/mL) for 1 hour at room temperature (RT) to convert all the soluble cellobiose to glucose. The amount of glucose released was then measured by adding 64 μL of glucose oxidase (1.25 U/mL), HRP (1.25 U/mL), and Amplex Red (60 μM) containing 125 mM phosphate buffer, pH 7.45, and incubating at RT for 10 minutes. The amount of resorufin formed corresponds to the amount of glucose present. The resorufin fluorescence was measured by excitation at 530 nm and emission detection at 590 nm.

As shown in FIGS. 12 (a) and (b), the identified TrEGI mutants with substitutions of glutamic acid, glutamine, lysine, alanine, or serine at G230 had increased activity compared to wild-type TrEGI in hydrolyzing Avicel® and IL-Avicel® at 50° C. Similarly, TrEGI triple mutants with mutations D113S, D115T, and substitutions of lysine, alanine, serine, arginine, glutamic acid, leucine, methionine, or threonine at G230 showed increased activity in hydrolyzing Avicel® and IL-Avicel® relative to wild-type TrEGI at temperatures of 50, 53, or 55° C. [FIGS. 12 (c) and (d)]. The improvement in activity of the different mutations ranged from about 1.5- to 5-fold over that of wild-type TrEGI.

A comparison of activity of the TrEGI mutants on different cellulosic substrates is shown in FIG. 13. The mutants tested had increased activity in hydrolyzing substrates relative to wild-type TrEGI. In comparison with TrEGI mutants with single amino acid substitutions at G230, TrEGI mutants with mutations at three amino acids (G230, D113, D115) had up to 2.5-fold increased activity [FIGS. 13 (b) and (c)].

Example 6

Mutant Thermostable Enzymes from Glycosyl Hydrolase Family 7

This example is targeted to the mutation of a glycosyl hydrolase family 7 enzyme to increase its thermostability relative to the wild-type, non-mutated enzyme. The different techniques used have been discussed earlier.

The first step is to align the polypeptide sequence of the enzyme with the sequence of SEQ ID NO: 1, thereby identifying the amino acid residues which align with amino acids 230, 113, and 115 of SEQ ID NO: 1.

The second step is to mutate one or more of these identified amino acids to serine, threonine, leucine, methionine, lysine, alanine, glutamine, glutamic acid, or arginine, or glycine. The mutated enzymes are then expressed and purified.

The third step is to measure thermostability of the mutated enzymes. The mutated enzymes are incubated at temperatures, such as between 50-70° C., for different lengths of time, e.g., between 15-60 minutes. This incubation is followed by assaying cellulase activity of the mutant enzymes. The assays can be carried out using a variety of cellulosic substrates. Wild-type versions of the enzymes are used as controls in the assays.

The mutated enzymes which are most active at high temperatures can be used in various industrial applications, such as biofuels production, food processing, textile cleaning, etc.

Example 7

Thermostable *T. reesei* EGI Mutants

This example tested the thermostability of the TrEGI mutants on different cellulosic substrates.

Expression of *T. reesei* EG1 in *S. cerevisiae*

For production of *T. reesei* EG1 and engineered mutants in *S. cerevisiae*, the genes were cloned after six histidine residues were appended to the C-terminus in the pCu424 vector (Labbe, S and Thiele, D J, *Methods Enzymol*. 1999, 306, 145-153). An engineered α-factor AppS4 signal peptide (Rakestraw, J A, et al., *Biotechnol. Bioeng*. 2009, 103, 1192-1201) was appended onto the N-terminus of the genes to enable secretion of the enzyme. The pCu424 vector containing the *T. reesei* EG1 gene was transformed into *S. cerevisiae* strain YVH10 (Robinson, A S et al., *Biotechnology (NY)* 1994, 12, 381-384) with an additional pmr1 knockout using the LiAc method (Gietz, R D and Schiestl, R H, *Nat. Protoc*. 2007, 2, 31-34. For expression, a saturated YPD medium preculture was used to inoculate 1 L selective medium (SC-Trp) and grown for three days at 30° C. The culture was spun down at 4000 g for 5 mM and resuspended in YPD medium supplemented with 500 μM CuSO$_4$ for a three day induction at 25° C. EGI was purified from culture supernatant using Ni affinity chromatography.

Trimming Glycosylation of *T. reesei* EG1 Expressed in *S. cerevisiae*

3-5 mg of purified *T. reesei* EG1 expressed in *S. cerevisiae* was incubated in pH 7.0 25 mM phosphate buffer along with 200 units of PNGaseF (NEB) at 30° C. for 18 h following which additional 100 units of PNGaseF were added and incubated for another 24 h. PNGaseF treated *T. reesei* EG1 was purified using gel filtration chromatography.

Thermostability of Cell-Free *T. reesei* EG1 Protein

Figure 14:
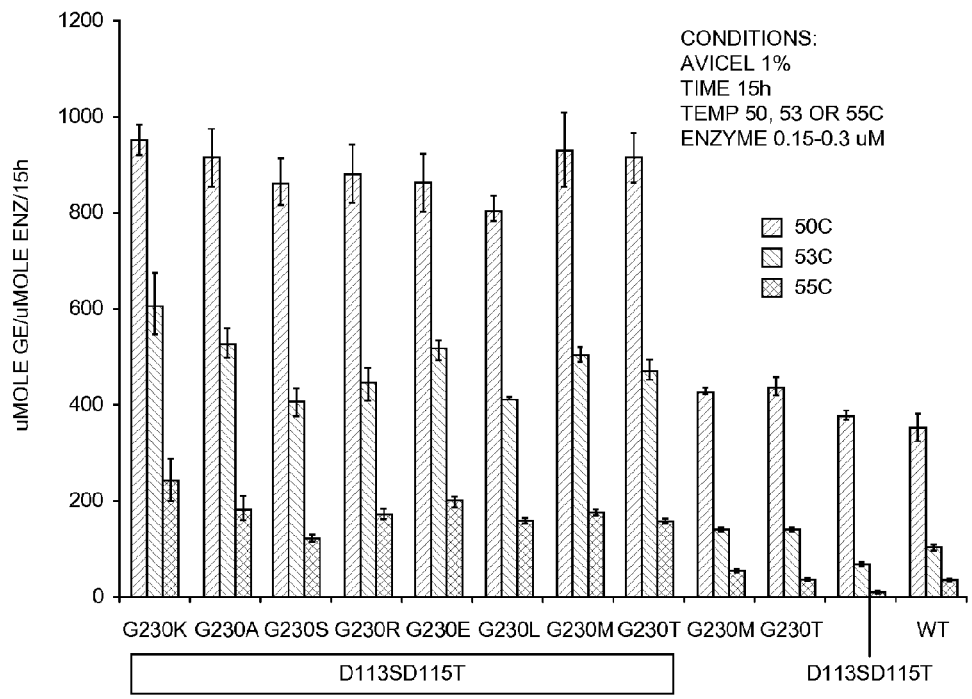
FIG. 14 shows the activity of cell free extracts of *T. reesei* EGI mutants on Avicel® at different temperatures. GE indicates "Glucose Equivalents".
Figure 15:
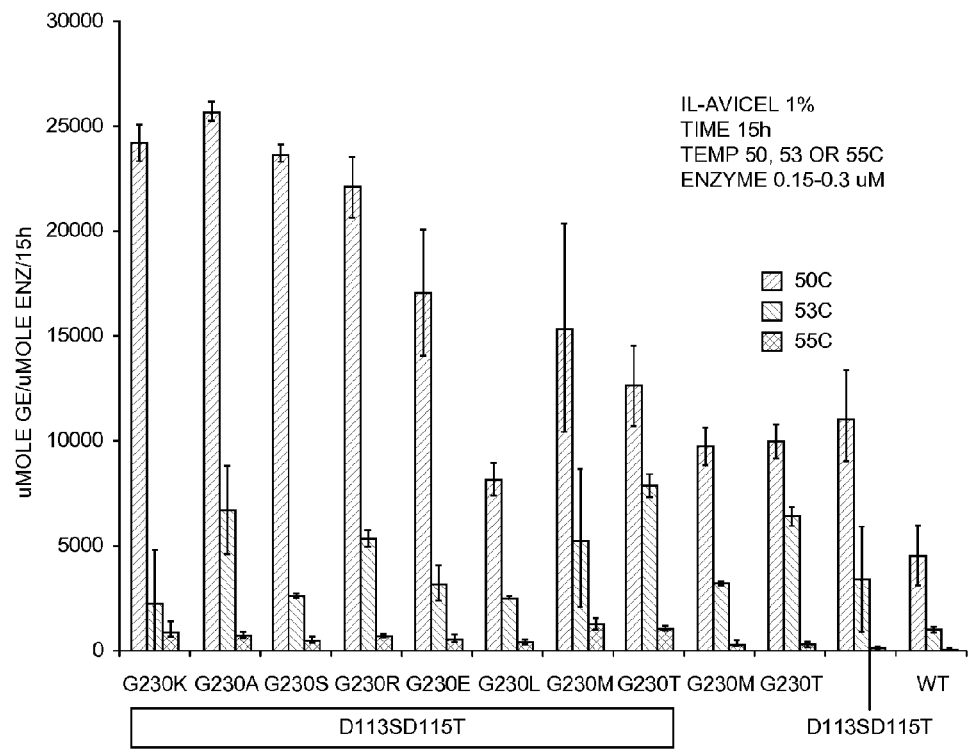
FIG. 15 shows the activity of cell free extracts of *T. reesei* EGI mutants on IL-Avicel® at different temperatures. GE indicates "Glucose Equivalents".

The *T. reesei* EGI mutants with various amino acid substitutions at the G230 site and D113D115 site were found to be more thermostable than the parent enzyme on Avicel® and IL-Avicel®, when expressed using cell-free protein synthesis based on *E. coli* cell-extract (which does not have the ability to glycosylate the enzymes). As shown in FIG. 14, the *T. reesei* EGI mutants have an approximately 2-fold improvement in activity on Avicel® at 50° C., compared to the parent enzyme. As shown in FIG. 15, the *T. reesei* EGI mutants have an approximately 5-fold improvement in activity on IL-Avicel® at 50° C., compared to the parent enzyme.

Thermostability of *T. reesei* EG1 Expressed in *S. cerevisiae*

Figure 16:
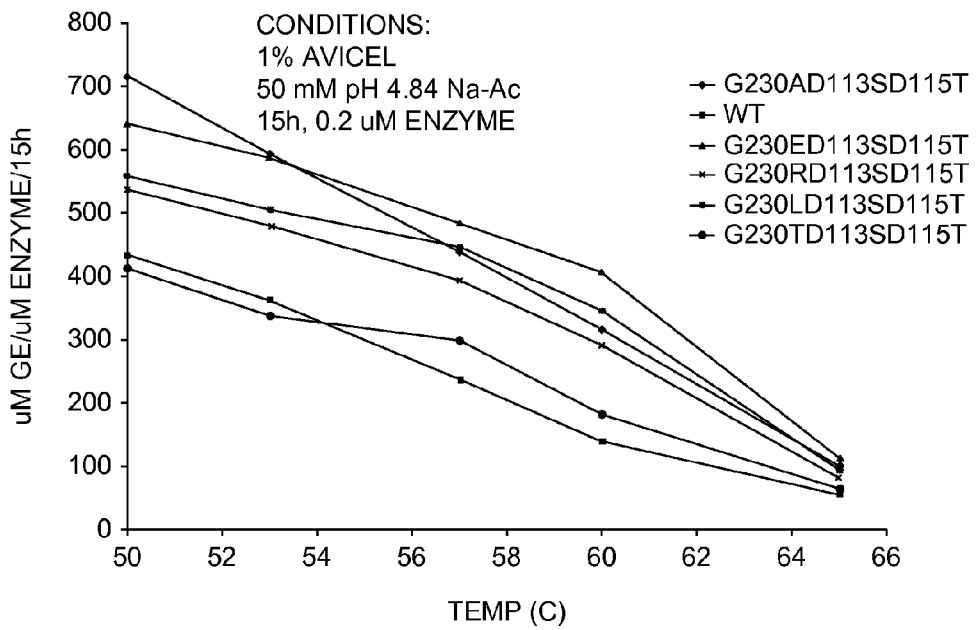
FIG. 16 shows the activity of *T. reesei* EGI mutants expressed in yeast with trimmed glycosylation on Avicel® at different temperatures. GE indicates "Glucose Equivalents".
Figure 17:
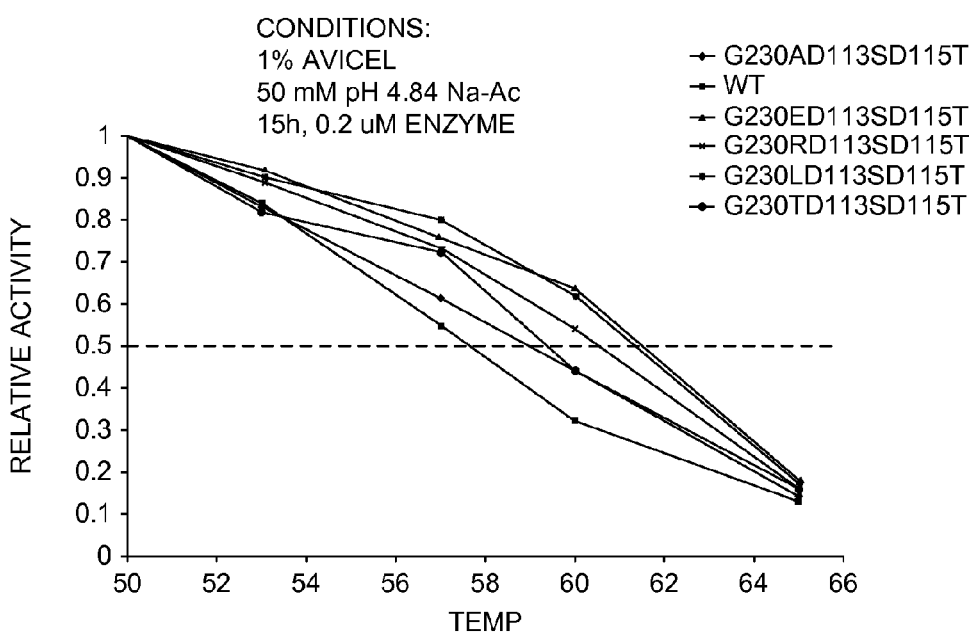
FIG. 17 shows the T50 of *T. reesei* EGI mutants expressed in yeast with trimmed glycosylation on Avicel®.
Figure 18:
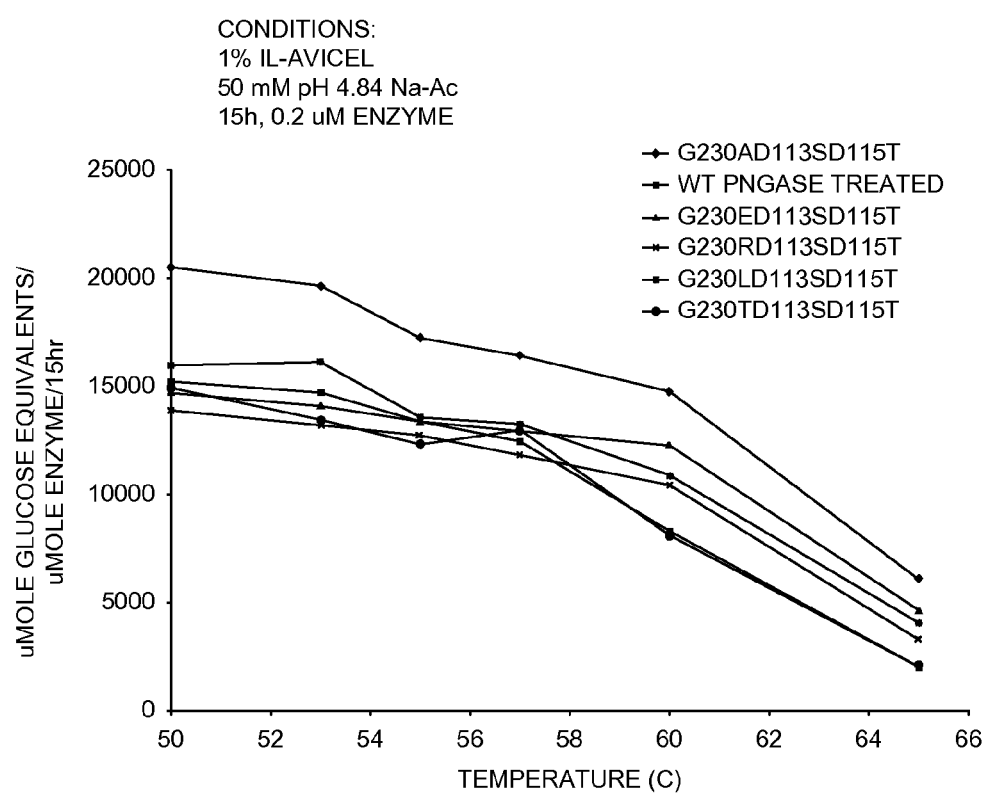
FIG. 18 shows the activity of *T. reesei* EGI mutants expressed in yeast with trimmed glycosylation on IL-Avicel® at different temperatures. GE indicates "Glucose Equivalents".

The thermostable *T. reesei* EGI mutants were expressed in yeast (*S. cerevisiae*) to study the impact of glycosylation of these enzyme variants on their activity/stability. Yeast expressed *T. reesei* EG1 mutants with various amino acids (A, E, R, L, T, and S) at the G230 site in combination with the D113SD15T mutation were purified using Ni-NTA chromatography. Due to the hyper glycosylation of these enzymes upon expression in yeast (MW 100-200 Kda), the N-glycosylation was trimmed using PNGaseF to obtain Tr EGI enzymes bearing glycosylation levels (MW~55-60 Kda) very similar to the native enzyme expressed in *T. reesei*. Activity measurements of these engineered enzymes with trimmed glycosylation showed improved activity on Avicel® and IL-Avicel® at temperatures from 50° C.-65° C. (FIGS. 16-18). The best mutant (G230AD113SD115T mutation) showed a 2.5-fold improvement in activity at 60° C. on Avicel® compared to the parent enzyme (FIG. 16), and a 2-fold improvement in activity at 65° C. on IL-Avicel® compared to the parent enzyme (FIG. 18). FIG. 17 shows that the G230AD113SD115T mutant had an approximately 4° C. increase in T50 on Avicel® compared to the parent enzyme (FIG. 17).

What is claimed is:

1. A mutant thermostable endoglucanase I enzyme, wherein the mutant thermostable enzyme has an amino acid substitution at position 230 of SEQ ID NO: 1 with an amino acid selected from the group consisting of
serine, threonine, leucine, methionine, lysine, alanine, glutamine, glutamic acid, and arginine; and
an amino acid substitution at position 113 of SEQ ID NO: 1 with an amino acid selected from the group consisting of leucine and serine.

2. A mutant thermostable endoglucanase I enzyme, wherein the mutant thermostable enzyme has
an amino acid substitution at position 230 of SEQ ID NO: 1 with an amino acid selected from the group consisting of serine, threonine, leucine, methionine, lysine, alanine, glutamine, glutamic acid, and arginine;
an amino acid substitution at position 113 of SEQ ID NO: 1 with an amino acid selected from the group consisting of leucine and serine; and
an amino acid substitution at position 115 of SEQ ID NO: 1 with an amino acid selected from the group consisting of threonine and glycine.

3. A mutant thermostable endoglucanase I enzyme, wherein the mutant thermostable enzyme has an amino acid substitution at position 230 of SEQ ID NO: 1 with an amino acid selected from the group consisting of serine, threonine, leucine, methionine, lysine, alanine, glutamine, glutamic acid, and arginine; and an amino acid substitution at position 115 of SEQ ID NO: 1 with an amino acid selected from the group consisting of threonine and glycine.

4. A mutant thermostable endoglucanase I enzyme, wherein the mutant thermostable enzyme has an amino acid substitution at position 113 of SEQ ID NO: 1 with an amino acid selected from the group consisting of leucine and serine; and an amino acid substitution at position 115 of SEQ ID NO: 1 with an amino acid selected from the group consisting of threonine and glycine.

5. The mutant thermostable enzyme of claim 1, wherein the enzyme exhibits increased thermostability as compared to the wild-type enzyme after incubation at about 50° C. for about one hour.

6. The mutant thermostable enzyme of claim 1, wherein the enzyme has a specific activity of at least about 0.5 mMole GE/μMole enzyme/hr after incubation at about 50° C. for about one hour.

7. A composition comprising the mutant thermostable enzyme of claim 1.

8. An isolated nucleic acid encoding the mutant thermostable enzyme of claim 1.

9. An expression vector comprising the nucleic acid of claim 8 operably linked to a regulatory sequence.

10. A host cell comprising the expression vector of claim 9.

11. A composition comprising the host cell of claim 10 and culture medium.

12. A method of reducing the viscosity of a pretreated biomass mixture, comprising:
contacting a pretreated biomass mixture having an initial viscosity with the composition of claim 7; and
incubating the contacted biomass mixture under conditions sufficient to reduce the initial viscosity of said pretreated biomass mixture.

13. A method of converting biomass to sugars comprising contacting the biomass with the composition of claim 7.

14. A method of hydrolyzing or degrading biomass, comprising contacting the biomass with the composition of claim 7.

15. A method of producing a fermentation product, comprising:
- contacting biomass with the composition of composition of claim 7 to form a first product; and
- culturing the first product with one or more fermentative microorganisms or a chemical solution under conditions sufficient to produce a fermentation product.

16. The method of claim 15, wherein the contacting is conducted at a temperature between about 50° C. and about 55° C., between about 55° C. and about 60° C., or between about 60° C. to about 70° C.

17. A method of fermenting biomass, comprising:
- contacting biomass with one or more fermentative microorganisms, wherein the biomass is treated by the composition of claim 7.

18. A method of producing a fuel comprising:
- contacting biomass with the composition of claim 7 to yield a sugar solution; and
- culturing the sugar solution with a fermentative microorganism or a chemical solution under conditions sufficient to produce a fuel.

19. The method of claim 18, wherein the contacting is conducted at a temperature between about 50° C. and about 55° C., between about 55° C. and about 60° C., or between about 60° C. to about 70° C.

* * * * *